US012790405B2

(12) United States Patent
Kielczewska et al.

(10) Patent No.: US 12,790,405 B2
(45) Date of Patent: Nov. 10, 2026

(54) MATERIALS AND METHODS FOR MONITORING CANCER BY ADMINISTERING AN ANTI-MCL1 ANTIBODY

(71) Applicant: AMGEN INC., Thousand Oaks, CA (US)

(72) Inventors: Agnieszka Kielczewska, Thousand Oaks, CA (US); Brian Chan, Thousand Oaks, CA (US); Michael C. Boyle, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 547 days.

(21) Appl. No.: 18/275,169

(22) PCT Filed: Jan. 28, 2022

(86) PCT No.: PCT/US2022/014401

§ 371 (c)(1),
(2) Date: Jul. 31, 2023

(87) PCT Pub. No.: WO2022/165240

PCT Pub. Date: Aug. 4, 2022

(65) Prior Publication Data

US 2024/0117069 A1 Apr. 11, 2024

Related U.S. Application Data

(60) Provisional application No. 63/143,682, filed on Jan. 29, 2021.

(51) Int. Cl.

| | |
|---|---|
| ***C07K 16/30*** | (2006.01) |
| ***A61K 31/553*** | (2006.01) |
| ***G01N 33/57505*** | (2026.01) |

(52) U.S. Cl.

CPC ........ *C07K 16/3061* (2013.01); *A61K 31/553* (2013.01); *G01N 33/57505* (2026.01)

(58) Field of Classification Search

None

See application file for complete search history.

(56) References Cited

U.S. PATENT DOCUMENTS

| | | | |
|---|---|---|---|
| 4,816,397 | A | 3/1989 | Boss et al. |
| 4,946,778 | A | 8/1990 | Ladner et al. |
| 5,151,510 | A | 9/1992 | Stec et al. |
| 5,260,203 | A | 11/1993 | Ladner et al. |
| 5,403,484 | A | 4/1995 | Ladner et al. |
| 5,545,806 | A | 8/1996 | Lonberg et al. |
| 5,569,825 | A | 10/1996 | Lonberg et al. |
| 5,571,698 | A | 11/1996 | Ladner et al. |
| 5,702,892 | A | 12/1997 | Mulligan-Kehoe |
| 5,714,352 | A | 2/1998 | Jakobobits et al. |
| 5,780,279 | A | 7/1998 | Matthews et al. |
| 5,821,047 | A | 10/1998 | Garrard et al. |
| 5,824,520 | A | 10/1998 | Mulligan-Kehoe |
| 5,837,500 | A | 11/1998 | Ladner et al. |
| 5,855,885 | A | 1/1999 | Smith et al. |
| 5,858,657 | A | 1/1999 | Winter et al. |
| 5,871,907 | A | 2/1999 | Winter et al. |
| 5,969,108 | A | 10/1999 | McCafferty et al. |
| 6,057,098 | A | 5/2000 | Buechler et al. |
| 6,225,447 | B1 | 5/2001 | Winter et al. |
| 6,265,150 | B1 | 7/2001 | Terstappen et al. |
| 9,562,061 | B2 | 2/2017 | Brown et al. |
| 10,300,075 | B2 | 5/2019 | Brown et al. |
| 2002/0086321 | A1 | 7/2002 | Craig |
| 2002/0197266 | A1 | 12/2002 | Debinski |
| 2009/0028784 | A1 | 1/2009 | Garcia-Martinez et al. |
| 2010/0040606 | A1 | 2/2010 | Lantto et al. |
| 2014/0178905 | A1 | 6/2014 | Walker et al. |
| 2017/0051071 | A1 | 2/2017 | Rueger et al. |
| 2020/0399373 | A1 | 12/2020 | Igawa et al. |

FOREIGN PATENT DOCUMENTS

| | | | |
|---|---|---|---|
| CN | 109813916 | A | 5/2019 |
| EP | 0281604 | B1 | 3/1993 |
| JP | 2020-115780 | A | 8/2020 |
| WO | 88/01649 | A1 | 3/1988 |
| WO | 2015/153657 | A2 | 10/2015 |
| WO | 2019/173692 | A2 | 9/2019 |

OTHER PUBLICATIONS

Akgul, Mcl-1 is a potential therapeutic target in multiple types of cancer, Cell. Mol. Life Sci., 66:1326-1336.

Burton et al., Human antibody effector function, Advances in Immunology, 51:1-84 (1992).

Cedeno-Arias et al., Validation of a flow cytometry based binding assay for evaluation of monoclonal antibody recognizing EGF receptor, Sci. Pharm., 79(3):569-581 (2011).

Chand et al., A competitive ELISA for detection of group specific antibody to bluetongue virus using anti-core antibody, Biologicals, 46:168-171 (2017).

Chothia et al., Canonical structures for the hypervariable regions of immunoglobulins, J. Mol. Biol., 196(4):901-917 (1987).

Chothia et al., Conformations of immunoglobulin hypervariable regions, Nature, 342:877-883 (1989).

Chu et al., SV40 DNA transfection of cells in suspension: analysis of efficiency of transcription and translation of T-antigen, Gene., 13:197-202 (1981).

(Continued)

*Primary Examiner* — Peter Johansen

(74) *Attorney, Agent, or Firm* — MARSHALL, GERSTEIN & BORUN LLP

(57) ABSTRACT

The disclosure provides anti-Mcl-1 antibodies of any form, and fragments thereof, that bind the antigen with unexpectedly high binding to Mcl-1, providing tools useful in methods of monitoring cancer cells expressing Mcl-1 and methods of treating cancers, particularly blood-borne cancers, comprising such cancer cells.

20 Claims, 24 Drawing Sheets

Specification includes a Sequence Listing.

(56) References Cited

OTHER PUBLICATIONS

Creighton, Proteins, Structures and Molecular Principles, W. H. Freeman and Company, New York, (1984).
Geuijen et al., Affinity ranking of antibodies using flow cytometry: Application in antibody phage display-based target discovery, J. Immunol. Methods, 302(1-2):68-77 (2005).
Goolia et al., Validation of a competitive ELISA and a virus neutralization test for the detection and confirmation of antibodies to Senecavirus A in swine sera, J. Vet. Diagn. Invest., 29(2):250-253 (2017).
Graham et al., A new technique for the assay of infectivity of human adenovirus 5 DNA, Virology, 52:456-467 (1973).
Haskard et al., The production of human monoclonal autoantibodies from patients with rheumatoid arthritis by the EBV-hybridoma technique, J. Immunol. Methods, 74(2):361-67 (1984).
Huse et al., Generation of a large combinatorial library of the immunoglobulin repertoire in phage lambda, Science, 246:1275-1281 (1989).
International Application No. PCT/US2022/014401, International Preliminary Report on Patentability, mailed Aug. 10, 2023.
International Application No. PCT/US2022/014401, International Search Report and Written Opinion, mailed Jun. 27, 2022.
International Application No. PCT/US2022/014401, Invitation to Pay Additional Fees, mailed Apr. 27, 2022.
Janeway et al., Immunobiology, 5th Ed., Garland Publishing, New York, (2001).
Laplanche et al., Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates, Nucl. Acids Res., 14:9081-93 (1986).
Lessene et al., BCL-2 family antagonists for cancer therapy, Nat. Rev. Drug. Discov., 7:989-1000 (2008).
Liu et al., Development of competitive ELISA for the detection of bovine serum albumin using single-chain variable fragments, Anal. Biochem., 525:89-91 (2017).
Mandelin et al., Myeloid cell leukemia-1 as a therapeutic target, Expert Opin. Ther. Targets, 11:363-373 (2007).
Medesan et al., Comparative studies of rat IgG to further delineate the Fc:FcRn interaction site, Eur. J. Immunol., 28:2092-2100 (1998).
Mullinax et al., Identification of human antibody fragment clones specific for tetanus toxoid in a bacteriophage lambda immunoexpression library, Proc. Natl. Acad. Sci. U. S. A., 87(20):8095-8099 (1990).
Orlandi et al., Cloning immunoglobulin variable domains for expression by the polymerase chain reaction, Proc. Natl. Acad. Sci. USA, 86(10):3833-3837 (1989).
Rathanaswami et al., High-affinity binding measurements of antibodies to cell-surface-expressed antigens, Analytical. Biochemistry, 373(1):52-60 (2008).
Ravetch et al., IgG Fc receptors, Annu. Rev. Imm., 19:275-90 (2001).
Roder et al., The EBV-hybridoma technique, Methods Enzymol., 121:140-67 (1986).
Sambrook et al., Molecular Cloning: a Laboratory Manual, 3rd Ed., Cold Spring Harbor, N.Y., (2001).
Shields et al., High resolution mapping of the binding site on human IgG1 for Fc gamma RI, Fc gamma RII, Fc gamma RIII, and FcRn and design of IgG1 variants with improved binding to the Fc gamma R, J. Biol. Chem., 276(9):6591-6604 (2001).
Spiess et al., Alternative molecular formats and therapeutic applications for bispecific antibodies, Mol. Immunol., 67(2 Part A):95-106 (2015).
Stec et al., Automated solid-phase synthesis, separation, and stereochemistry of phosphorothioate analogs of oligodeoxyribonucleotides, J. Am. Chem. Soc., 106:6077-79 (1984).
Stein et al., Physicochemical properties of phosphorothioate oligodeoxynucleotides, Nucl. Acid. Res., 16:3209-21 (1988).
Structural Genomics Consortium, Protein production and purification, Nat Methods, 5(2):135-146 (2008).
Tam et al., Abciximab (ReoPro, chimeric 7E3 Fab) demonstrates equivalent affinity and functional blockade of glycoprotein IIb/IIIa and alpha(v)beta3 integrins, Circulation, 98(11):1085-1091 (1998).
Telleman et al., The role of the Brambell receptor (FcRB) in liver: protection of endocytosed immunoglobulin G (IgG) from catabolismin hepatocytes rather than transport of IgG to bile, Immunology, 100:245-251 (2000).
Thornton et al., Protein structure. Prediction of progress at last, Nature, 354:105-6 (1991).
Trikha et al., CNTO 95, a fully human monoclonal antibody that inhibits alphav integrins, has antitumor and antiangiogenic activity in vivo, Int. J. Cancer, 110:326-335 (2004).
Uhlmann et al., Antisense oligonucleotides: a new therapeutic principle, Chem. Rev., 90(4):543-584 (1990).
Winter et al., Man-made antibodies, Nature, 349:293-299 (1991).
Zon et al., Oligonucleotides and Analogues: a Practical Approach, Oxford University Press, Oxford England, 87-108 (1991).
Zon et al., Phosphorothioate oligonucleotides: chemistry, purification, analysis, scale-up and future directions, Anti-Cancer Drug Design, 6:539-68 (1991).

A B C D E F G H

A B C

| | Cell Line ID | Tumor Type | BCL2 | BCLXL | MCL1 |
|---|---|---|---|---|---|
| AMO1 | 1-1 | Multiple Myeloma | 2 | 8 | 1 |
| RPMI8226 | 2-1 | Multiple Myeloma | 3 | 4 | 3 |
| DMS-273 | 3-1 | Small Cell Lung | 6 | 6 | 2 |
| G361 | 4-1 | Melanoma | 5 | 2 | 6 |
| COLO205 | 5-1 | Colorectal | 8 | 3 | 7 |
| OPM2 | 6-1 | Multiple Myeloma | 4 | 5 | 5 |
| AGS | 7-1 | Gastric | 7 | 1 | 4 |
| SKMM2 | 8-1 | Multiple Myeloma | 1 | 7 | 8 |

SEQUENCE LISTING

```
<160> NUMBER OF SEQ ID NOS: 39

<210> SEQ ID NO 1
<211> LENGTH: 39
<212> TYPE: DNA
<213> ORGANISM: Artificial Sequence
<220> FEATURE:
<223> OTHER INFORMATION: Synthetic

<400> SEQUENCE: 1

caagctagcc agtctttata caacaacaac tatttaggc                           39


<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2

caagctagca agctggccag c                                              21


<210> SEQ ID NO 3
<211> LENGTH: 30
<212> TYPE: DNA
<213> ORGANISM: Artificial Sequence
<220> FEATURE:
<223> OTHER INFORMATION: Synthetic

<400> SEQUENCE: 3

gccggtttag acaacgacga catcttcagc                                     30
```

-continued

```
<210> SEQ ID NO 4
<211> LENGTH: 13
<212> TYPE: PRT
<213> ORGANISM: Artificial Sequence
<220> FEATURE:
<223> OTHER INFORMATION: Synthetic

<400> SEQUENCE: 4

Gln Ala Ser Gln Ser Leu Tyr Asn Asn Asn Tyr Leu Gly
1               5                   10


<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Gln Ala Ser Lys Leu Ala Ser
1               5


<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Ala Gly Leu Asp Asn Asp Asp Ile Phe Ser
1               5                   10


<210> SEQ ID NO 7
<211> LENGTH: 39
<212> TYPE: DNA
<213> ORGANISM: Artificial Sequence
<220> FEATURE:
<223> OTHER INFORMATION: Synthetic

<400> SEQUENCE: 7

cagagcagcc agaccgtgta caacaacaac gatttagct                            39


<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8

gatgccagcg atctgcccag c                                               21


<210> SEQ ID NO 9
<211> LENGTH: 39
<212> TYPE: DNA
<213> ORGANISM: Artificial Sequence
<220> FEATURE:
<223> OTHER INFORMATION: Synthetic

<400> SEQUENCE: 9

ttaggaggct acgactgcgt gagcggcgac tgcattgcc                            39


<210> SEQ ID NO 10
<211> LENGTH: 13
```

<212> TYPE: PRT
<213> ORGANISM: Artificial Sequence
<220> FEATURE:
<223> OTHER INFORMATION: Synthetic

<400> SEQUENCE: 10

Gln Ser Ser Gln Thr Val Tyr Asn Asn Asn Asp Leu Ala
1 5 10

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Asp Ala Ser Asp Leu Pro Ser
1 5

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Leu Gly Gly Tyr Asp Cys Val Ser Gly Asp Cys Ile Ala
1 5 10

<210> SEQ ID NO 13
<211> LENGTH: 15
<212> TYPE: DNA
<213> ORGANISM: Artificial Sequence
<220> FEATURE:
<223> OTHER INFORMATION: Synthetic

<400> SEQUENCE: 13
cgtttcggca ttagc 15

<210> SEQ ID NO 14
<211> LENGTH: 48
<212> TYPE: DNA
<213> ORGANISM: Artificial Sequence
<220> FEATURE:
<223> OTHER INFORMATION: Synthetic

<400> SEQUENCE: 14
atcatctctc gtaacgacat cacctactac gccaactggg ccaagggt 48

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
ggcggccccg gctattccga tagcagcgtg 30

<210> SEQ ID NO 16
<211> LENGTH: 5
<212> TYPE: PRT
<213> ORGANISM: Artificial Sequence
<220> FEATURE:
<223> OTHER INFORMATION: Synthetic

<400> SEQUENCE: 16

Arg Phe Gly Ile Ser
1               5

<210> SEQ ID NO 17
<211> LENGTH: 16
<212> TYPE: PRT
<213> ORGANISM: Artificial Sequence
<220> FEATURE:
<223> OTHER INFORMATION: Synthetic

<400> SEQUENCE: 17

Ile Ile Ser Arg Asn Asp Ile Thr Tyr Tyr Ala Asn Trp Ala Lys Gly
1               5                   10                  15

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Gly Gly Pro Gly Tyr Ser Asp Ser Ser Val
1               5                   10

<210> SEQ ID NO 19
<211> LENGTH: 15
<212> TYPE: DNA
<213> ORGANISM: Artificial Sequence
<220> FEATURE:
<223> OTHER INFORMATION: Synthetic

<400> SEQUENCE: 19
acccacacca tcatc 15

<210> SEQ ID NO 20
<211> LENGTH: 48
<212> TYPE: DNA
<213> ORGANISM: Artificial Sequence
<220> FEATURE:
<223> OTHER INFORMATION: Synthetic

<400> SEQUENCE: 20
atcatctacg acgtgggcgg cacctattac gccagctggg ctcgtggt 48

<210> SEQ ID NO 21
<211> LENGTH: 9
<212> TYPE: DNA
<213> ORGANISM: Artificial Sequence
<220> FEATURE:
<223> OTHER INFORMATION: Synthetic

<400> SEQUENCE: 21 tacggcatc 9

<210> SEQ ID NO 22
<211> LENGTH: 5
<212> TYPE: PRT
<213> ORGANISM: Artificial Sequence
<220> FEATURE:
<223> OTHER INFORMATION: Synthetic

<400> SEQUENCE: 22

Thr His Thr Ile Ile

-continued 1 5

<210> SEQ ID NO 23
<211> LENGTH: 16
<212> TYPE: PRT
<213> ORGANISM: Artificial Sequence
<220> FEATURE:
<223> OTHER INFORMATION: Synthetic

<400> SEQUENCE: 23

Ile Ile Tyr Asp Val Gly Gly Thr Tyr Tyr Ala Ser Trp Ala Arg Gly
1 5 10 15

<210> SEQ ID NO 24
<211> LENGTH: 3
<212> TYPE: PRT
<213> ORGANISM: Artificial Sequence
<220> FEATURE:
<223> OTHER INFORMATION: Synthetic

<400> SEQUENCE: 24

Tyr Gly Ile
1

<210> SEQ ID NO 25
<211> LENGTH: 330
<212> TYPE: DNA
<213> ORGANISM: Artificial Sequence
<220> FEATURE:
<223> OTHER INFORMATION: Synthetic

<400> SEQUENCE: 25
gcccaagttc tgacccagac cccttccagc gtgagcgctg ccgtgggcgg aacagtgacc 60
atcaactgcc aagctagcca gtctttatac aacaacaact atttaggctg gtaccagcag 120
aaggccggac agagccccaa gctgctgatc taccaagcta gcaagctggc cagcggagtg 180
cctagccagt tcaagggcag cggcagcggc accgacttta ctttaaccat caccgatgtg 240
cagtgcgacg acgccggcac ctattactgc gccggtttag acaacgacga catcttcagc 300
tttggcggcg gcaccgaggt ggtggtgagg 330

<210> SEQ ID NO 26
<211> LENGTH: 348
<212> TYPE: DNA
<213> ORGANISM: Artificial Sequence
<220> FEATURE:
<223> OTHER INFORMATION: Synthetic

<400> SEQUENCE: 26
cagagcgtga aggagagcgg cggcggttta ttcaagccta ccgacacttt aactttaact 60
tgtaccgtga gcggcatcga tttatctcgt ttcggcatta gctgggtgag acaagctccc 120
ggtaaaggtt tagagtggat cggcatcatc tctcgtaacg acatcaccta ctacgccaac 180
tgggccaagg gtcgtgtgac catcagcaag cccagcagca ccaccgtgga tttaaagctg 240
accagcccta ccaccgagga caccgccacc tacttctgcg tgagaggcgg ccccggctat 300
tccgatagca gcgtgtgggg acccggtact ttagtgaccg tgtcttta 348

<210> SEQ ID NO 27
<211> LENGTH: 110
<212> TYPE: PRT
<213> ORGANISM: Artificial Sequence
<220> FEATURE:
<223> OTHER INFORMATION: Synthetic

<400> SEQUENCE: 27

```
Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Leu Tyr Asn Asn
            20                  25                  30

Asn Tyr Leu Gly Trp Tyr Gln Gln Lys Ala Gly Gln Ser Pro Lys Leu
        35                  40                  45

Leu Ile Tyr Gln Ala Ser Lys Leu Ala Ser Gly Val Pro Ser Gln Phe
    50                  55                  60

Lys Gly Ser Gly Ser Gly Thr Asp Phe Thr Leu Thr Ile Thr Asp Val
65                  70                  75                  80

Gln Cys Asp Asp Ala Gly Thr Tyr Tyr Cys Ala Gly Leu Asp Asn Asp
                85                  90                  95

Asp Ile Phe Ser Phe Gly Gly Gly Thr Glu Val Val Val Arg
            100                 105                 110
```

<210> SEQ ID NO 28
<211> LENGTH: 116
<212> TYPE: PRT
<213> ORGANISM: Artificial Sequence
<220> FEATURE:
<223> OTHER INFORMATION: Synthetic

<400> SEQUENCE: 28

```
Gln Ser Val Lys Glu Ser Gly Gly Gly Leu Phe Lys Pro Thr Asp Thr
1               5                   10                  15

Leu Thr Leu Thr Cys Thr Val Ser Gly Ile Asp Leu Ser Arg Phe Gly
            20                  25                  30

Ile Ser Trp Val Arg Gln Ala Pro Gly Lys Gly Leu Glu Trp Ile Gly
        35                  40                  45

Ile Ile Ser Arg Asn Asp Ile Thr Tyr Tyr Ala Asn Trp Ala Lys Gly
    50                  55                  60

Arg Val Thr Ile Ser Lys Pro Ser Ser Thr Thr Val Asp Leu Lys Leu
65                  70                  75                  80

Thr Ser Pro Thr Thr Glu Asp Thr Ala Thr Tyr Phe Cys Val Arg Gly
                85                  90                  95

Gly Pro Gly Tyr Ser Asp Ser Ser Val Trp Gly Pro Gly Thr Leu Val
            100                 105                 110

Thr Val Ser Leu
        115
```

<210> SEQ ID NO 29
<211> LENGTH: 339
<212> TYPE: DNA
<213> ORGANISM: Artificial Sequence
<220> FEATURE:
<223> OTHER INFORMATION: Synthetic

<400> SEQUENCE: 29

```
gcccaagttc tgacccagac ccctagcagc gtgtccgctg ctgtgggcgg aaccgtgacc      60

atcaactgcc agagcagcca gaccgtgtac aacaacaacg atttagcttg gtaccagcag     120

aagcccggcc agcctcccaa gctgctgatc tacgatgcca gcgatctgcc cagcggcgtg     180

cctagcagat ttagcggcag cggcagcggc accgatttca ctttaaccat ctccgacgtg     240

cagtgcgatg acgccgccac ctactactgt ttaggaggct acgactgcgt gagcggcgac     300

tgcattgcct tcggaggcgg caccgaggtg gtggtgaag                            339
```

-continued

<210> SEQ ID NO 30
<211> LENGTH: 324
<212> TYPE: DNA
<213> ORGANISM: Artificial Sequence
<220> FEATURE:
<223> OTHER INFORMATION: Synthetic

<400> SEQUENCE: 30
cagtctttag aggagagcgg aggcagactg gtgacccccg gtacacctct gactttaact 60
tgtaccgcca gcggctttac catcagcacc cacaccatca tctgggtgag acaagctccc 120
ggtaagggtt tagagtacat cggcatcatc tacgacgtgg gcggcaccta ttacgccagc 180
tgggctcgtg gtcgtttcac catcagcaag accagcacca ccgtggattt aaagatcacc 240
agccccacca ccgaggatac cgccacctac ttctgtaccg gctacggcat ctggggaccc 300
ggtactttag tgacagtgtc ttta 324

<210> SEQ ID NO 31
<211> LENGTH: 113
<212> TYPE: PRT
<213> ORGANISM: Artificial Sequence
<220> FEATURE:
<223> OTHER INFORMATION: Synthetic

<400> SEQUENCE: 31

Ala Gln Val Leu Thr Gln Thr Pro Ser Ser Val Ser Ala Ala Val Gly
1 5 10 15

Gly Thr Val Thr Ile Asn Cys Gln Ser Ser Gln Thr Val Tyr Asn Asn
20 25 30

Asn Asp Leu Ala Trp Tyr Gln Gln Lys Pro Gly Gln Pro Pro Lys Leu
35 40 45

Leu Ile Tyr Asp Ala Ser Asp Leu Pro Ser Gly Val Pro Ser Arg Phe
50 55 60

Ser Gly Ser Gly Ser Gly Thr Asp Phe Thr Leu Thr Ile Ser Asp Val
65 70 75 80

Gln Cys Asp Asp Ala Ala Thr Tyr Tyr Cys Leu Gly Gly Tyr Asp Cys
85 90 95

Val Ser Gly Asp Cys Ile Ala Phe Gly Gly Gly Thr Glu Val Val Val
100 105 110

Lys

<210> SEQ ID NO 32
<211> LENGTH: 108
<212> TYPE: PRT
<213> ORGANISM: Artificial Sequence
<220> FEATURE:
<223> OTHER INFORMATION: Synthetic

<400> SEQUENCE: 32

Gln Ser Leu Glu Glu Ser Gly Gly Arg Leu Val Thr Pro Gly Thr Pro
1 5 10 15

Leu Thr Leu Thr Cys Thr Ala Ser Gly Phe Thr Ile Ser Thr His Thr
20 25 30

Ile Ile Trp Val Arg Gln Ala Pro Gly Lys Gly Leu Glu Tyr Ile Gly
35 40 45

Ile Ile Tyr Asp Val Gly Gly Thr Tyr Tyr Ala Ser Trp Ala Arg Gly
50 55 60

Arg Phe Thr Ile Ser Lys Thr Ser Thr Thr Val Asp Leu Lys Ile Thr 65 70 75 80

Ser Pro Thr Thr Glu Asp Thr Ala Thr Tyr Phe Cys Thr Gly Tyr Gly
85 90 95

Ile Trp Gly Pro Gly Thr Leu Val Thr Val Ser Leu
100 105

<210> SEQ ID NO 33
<211> LENGTH: 350
<212> TYPE: PRT
<213> ORGANISM: Homo Sapiens
<220> FEATURE:
<221> NAME/KEY: MISC_FEATURE
<222> LOCATION: (29)..(47)
<223> OTHER INFORMATION: Peptide Design 1
<220> FEATURE:
<221> NAME/KEY: MISC_FEATURE
<222> LOCATION: (123)..(139)
<223> OTHER INFORMATION: Peptide Design 4
<220> FEATURE:
<221> NAME/KEY: MISC_FEATURE
<222> LOCATION: (148)..(166)
<223> OTHER INFORMATION: Peptide Design 6
<220> FEATURE:
<221> NAME/KEY: MISC_FEATURE
<222> LOCATION: (169)..(188)
<223> OTHER INFORMATION: Peptide Design 2
<220> FEATURE:
<221> NAME/KEY: MISC_FEATURE
<222> LOCATION: (169)..(188)
<223> OTHER INFORMATION: Peptide Design 2
<220> FEATURE:
<221> NAME/KEY: MISC_FEATURE
<222> LOCATION: (209)..(224)
<223> OTHER INFORMATION: BH3
<220> FEATURE:
<221> NAME/KEY: MISC_FEATURE
<222> LOCATION: (227)..(246)
<223> OTHER INFORMATION: Peptide Design 5
<220> FEATURE:
<221> NAME/KEY: MISC_FEATURE
<222> LOCATION: (252)..(271)
<223> OTHER INFORMATION: BH1
<220> FEATURE:
<221> NAME/KEY: MISC_FEATURE
<222> LOCATION: (252)..(271)
<223> OTHER INFORMATION: BH1
<220> FEATURE:
<221> NAME/KEY: MISC_FEATURE
<222> LOCATION: (271)..(271)
<223> OTHER INFORMATION: End of Isoform 1
<220> FEATURE:
<221> NAME/KEY: MISC_FEATURE
<222> LOCATION: (302)..(319)
<223> OTHER INFORMATION: Peptide Design 3
<220> FEATURE:
<221> NAME/KEY: MISC_FEATURE
<222> LOCATION: (303)..(316)
<223> OTHER INFORMATION: BH2
<220> FEATURE:
<221> NAME/KEY: MISC_FEATURE
<222> LOCATION: (328)..(348)
<223> OTHER INFORMATION: Transmembrane

<400> SEQUENCE: 33

Met Phe Gly Leu Lys Arg Asn Ala Val Ile Gly Leu Asn Leu Tyr Cys
1 5 10 15

Gly Gly Ala Gly Leu Gly Ala Gly Ser Gly Gly Ala Thr Arg Pro Gly
20 25 30

Gly Arg Leu Leu Ala Thr Glu Lys Glu Ala Ser Ala Arg Arg Glu Ile
35 40 45

Gly Gly Gly Glu Ala Gly Ala Val Ile Gly Gly Ser Ala Gly Ala Ser
50 55 60

-continued

```
Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Glu Leu Asp Gly
        115                 120                 125

Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160

Pro Ser Thr Pro Pro Pro Ala Glu Glu Glu Glu Asp Asp Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205

Ala Leu Glu Thr Leu Arg Arg Val Gly Asp Gly Val Gln Arg Asn His
    210                 215                 220

Glu Thr Ala Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
            260                 265                 270

Phe Val Ala Lys His Leu Lys Thr Ile Asn Gln Glu Ser Cys Ile Glu
        275                 280                 285

Pro Leu Ala Glu Ser Ile Thr Asp Val Leu Val Arg Thr Lys Arg Asp
    290                 295                 300

Trp Leu Val Lys Gln Arg Gly Trp Asp Gly Phe Val Glu Phe Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
            340                 345                 350


<210> SEQ ID NO 34
<211> LENGTH: 12
<212> TYPE: DNA
<213> ORGANISM: Oryctolagus cuniculus

<400> SEQUENCE: 34

ccaggtgacg gt                                                          12


<210> SEQ ID NO 35
<211> LENGTH: 24
<212> TYPE: DNA
<213> ORGANISM: Oryctolagus cuniculus

<400> SEQUENCE: 35

aggaacccag catggacact cgaa                                             24


<210> SEQ ID NO 36
<211> LENGTH: 30
<212> TYPE: DNA
```

-continued

```
<213> ORGANISM: Oryctolagus cuniculus

<400> SEQUENCE: 36

ggatcaggat atttattctg ccacgacaca                                     30


<210> SEQ ID NO 37
<211> LENGTH: 12
<212> TYPE: DNA
<213> ORGANISM: Oryctolagus cuniculus

<400> SEQUENCE: 37

tgcccgagtt cc                                                        12


<210> SEQ ID NO 38
<211> LENGTH: 21
<212> TYPE: DNA
<213> ORGANISM: Oryctolagus cuniculus

<400> SEQUENCE: 38

agacgactca ccatggagac t                                              21


<210> SEQ ID NO 39
<211> LENGTH: 17
<212> TYPE: DNA
<213> ORGANISM: Oryctolagus cuniculus

<400> SEQUENCE: 39

actggctccg ggaggta                                                   17
```

MATERIALS AND METHODS FOR MONITORING CANCER BY ADMINISTERING AN ANTI-MCL1 ANTIBODY

CROSS-REFERENCE TO RELATED APPLICATIONS

This application claims the priority benefit under 35 U.S.C. § 119(e) of U.S. Provisional Patent Application No. 63/143,682, filed Jan. 29, 2021, which is incorporated herein by reference in its entirety.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "55149_Seqlisting.txt", which was created on Jan. 28, 2022 and is 16,178 bytes in size. The subject matter of the Sequence Listing is incorporated herein in its entirety by reference.

FIELD

The disclosure provides materials and methods relating to monitoring immunotherapies and, in particular, to monitoring cancer immunotherapies.

BACKGROUND

Overexpression of induced Myeloid Leukemia Protein 1 (Mcl-1) is a common characteristic of human cancer. Mcl-1 overexpression prevents cancer cells from undergoing programmed cell death (apoptosis), allowing the cells to survive despite widespread genetic damage. Mcl-1 is a member of the Bcl-2 family of proteins. The Bcl-2 family includes pro-apoptotic members (such as BAX and BAK) which, upon activation, form homo-oligomers in the outer mitochondrial membrane that lead to pore formation and the escape of mitochondrial contents, a step in triggering apoptosis. Antiapoptotic members of the Bcl-2 family (such as Bcl-2, Bcl-xL, and Mcl-1) block the activity of BAX and BAK. Other proteins (such as BID, BIM, BIK, and BAD) exhibit additional regulatory functions.

Research has shown that Mcl-1 inhibitors can be useful for the treatment of cancers. Mcl-1 is overexpressed in numerous cancers. See Beroukhim et al., Nature 463:899-890 (2010). Cancer cells containing amplifications surrounding the Mcl-1 and Bcl-2-1-1 antiapoptotic genes depend on the expression of these genes for survival. Beroukhim et al. Mcl-1 is a relevant target for the re-initiation of apoptosis in numerous cancer cells. See Lessene et al., Nat. Rev. Drug. Discov., 7:989-1000 (2008); Akgul, Cell. Mol. Life Sci. 66 (2009); and Mandelin et al., Expert Opin. Ther. Targets 11:363-373 (2007).

The vertebrate immune system is known to be capable of producing an immune response characterized by production of an antibody that specifically binds, or recognizes, a precise antigen. The development of monoclonal antibodies and the proliferation of antibody forms have led to antibody technology becoming a significant weapon in the effort to combat specific diseases and disorders while minimizing the side effects commonly associated with non-specific therapeutics. The compound, (1S,3'R,6'R,7'S,8'E,11S,12'R)-6-chloro-7'-methoxy-11',12'-dimethyl-3,4-dihydro-2H,15'H-spiro[naphthalene-11',12'[20]oxa[13]thia[1,14]diazatetracyclo [14.7.2.$0^{3,6}$.$0^{19,24}$]pentacosa[8,16,18,24]tetraen]-15'-one 13',13'-dioxide (AMG 176), is useful as an inhibitor of myeloid cell leukemia 1 (Mcl-1). This compound has the formula I.

(I)

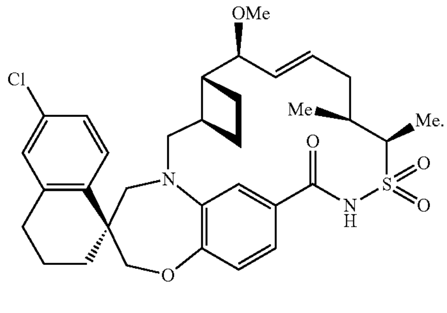

The compound, (1S,3'R,6'R,7'R,8'E,11'S,12'R)-6-chloro-7'-methoxy-11',12'-dinethyl-7'-((9aR)-octahydro-2H-pyrido [1,2-a]pyrazin-2-ylmethyl)-3,4-dihydro-2H,15'H-spiro [naphthalene-1,22'-[20]oxa[13]thia[1,14]diazatetracyclo [14.7.2.$0^{3,6}$.$0^{19,24}$] pentacosa[8,16,18,24]tetraen]-15'-one 13',13'-dioxide (AMG 397), is also useful as an inhibitor of myeloid cell leukemia 1 (Mcl-1). This compound has the formula II (II)

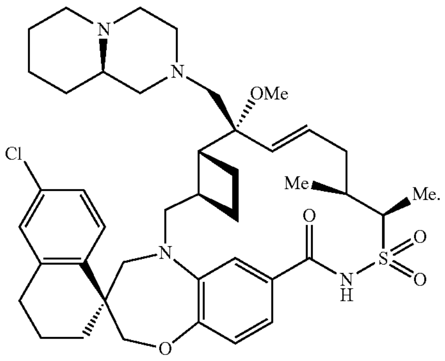

U.S. Pat. No. 9,562,061, which is incorporated herein by reference in its entirety, discloses AMG 176 as an Mcl-1 inhibitor and provides a method for preparing it.

U.S. Pat. No. 10,300,075, which is incorporated herein by reference in its entirety, discloses AMG 397 as an Mcl-1 inhibitor and provides a method for preparing it.

Although new compounds that modulate Mcl-1 have been disclosed, new antibodies and antibody formulations are needed to monitor the progress of efforts to inhibit MCL-1, for example in anti-cancer therapies.

SUMMARY

The disclosure provides antigen binding proteins such as antibodies of any form and fragments thereof that exhibit unexpectedly high binding properties (e.g., affinity, avidity, and sensitivity) towards the Mcl-1 antigen. Comparative tests showed that various commercial immunohistochemical (IHC) antibodies to Mcl-1 failed to detect Mcl-1 levels useful in monitoring cancer treatment. Mcl-1 is an induced myeloid leukemia cell differentiation protein from the Bcl-2 family found overexpressed in a variety of hematological and organ-based cancers. With the antigen binding proteins of the disclosure, methods of monitoring cancer treatments by measuring the levels of Mcl-1 over time have become feasible. It is contemplated that the disclosed methods of monitoring the treatment of cancers characterized by cells overexpressing Mcl-1 will be useful to monitor any cancer treatment targeting such cancers. Exemplary cancer treatments targeting such cancers include AMG 176 or AMG 397, both of which are Mcl-1 inhibitors. Detection of Mcl-1 expression can provide an indication of pharmacological response to the cancer treatment, such as the administration of AMG 176. AMG 176 has a core structure of formula (I)

(I)

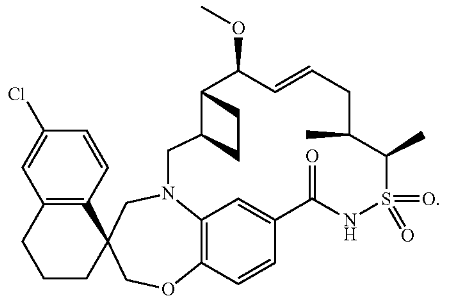

The structure of AMG 397, another Mcl-1 inhibitor, is shown in formula II.

(II)

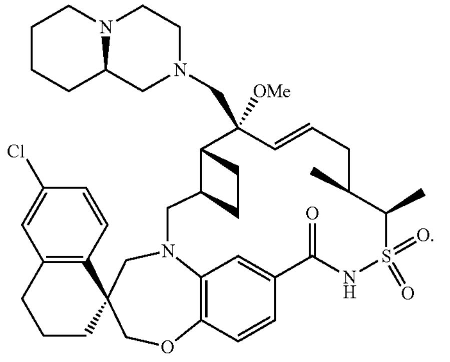

In one aspect, the disclosure provides an anti-Mcl-1 antibody or antigen-binding fragment thereof comprising the light chain complementarity determining region 1 (LCDR1) of SEQ ID NO:4, the light chain complementarity determining region 2 (LCDR2) of SEQ ID NO:5, the light chain complementarity determining region 3 of (LCDR3) SEQ ID NO:6, the heavy chain complementarity determining region 1 of SEQ ID NO:16 (HCDR1), the heavy chain complementarity determining region 2 of SEQ ID NO:17 (HCDR2), and the heavy chain complementarity determining region 3 of SEQ ID NO:18 (HCDR3), or comprising LCDR1 of SEQ ID NO:10, LCDR2 of SEQ ID NO:11, LCDR3 of SEQ ID NO:12, HCDR1 of SEQ ID NO:22, HCDR2 of SEQ ID NO:23, and HCDR3 of SEQ ID NO:24. In some embodiments, the antibody comprises the light chain variable region sequence of SEQ ID NO:27 or SEQ ID NO:31. In some embodiments, the antibody comprises the heavy chain variable region sequence of SEQ ID NO:28 or SEQ ID NO:32, including some embodiments in which the antibody further comprises the light chain variable region sequence of SEQ ID NO:27 if the heavy chain variable region sequence is set forth in SEQ ID NO:28, or SEQ ID NO:31 if the heavy chain variable region sequence is set forth in SEQ ID NO:32. In some embodiments, the antibody or fragment is a single-chain antibody or fragment, including embodiments in which the antibody fragment is contained in a single-chain variable fragment (scFv). In some embodiments, the antibody fragment is (a) a scFv; (b) a Fab; or (c) a (Fab')2. In some embodiments, the antibody or fragment thereof is fully human. In some embodiments, the antibody or fragment thereof is an immunoglobulin G (IgG) isotype antibody or fragment. In some embodiments, the antibody or fragment thereof is in the form of a monoclonal antibody. In some embodiments, the antibody or fragment thereof is in the form of a bispecific antibody, a trispecific antibody, a single chain variable fragment (scFv), a disulfide-bond-stabilized single chain variable fragment (ds-scFv), a single domain antibody (sdAb), a single chain Fab fragment (scFab), a diabody, a triabody, a tetrabody, a minibody, a Fab, a $F(ab')_2$, a VHH/VH fragment, a peptibody, a chimeric antigen receptor (CAR), or a bispecific T-cell engager (BiTE).

Another aspect of the disclosure is a pharmaceutical composition comprising a pharmaceutically acceptable carrier and a therapeutically effective amount of the antibody or an antigen-binding or an immunologically functional immunoglobulin fragment thereof that is disclosed herein.

Yet another aspect of the disclosure is a method of monitoring treatment of a cancer cell in a subject comprising: (a) contacting the cell of the subject with the antibody or fragment thereof of claim 1; (b) detecting binding of the antibody or fragment thereof to the cell or its contents; (c) determining the level of Mcl-1 in the cell; and (d) comparing the level of Mcl-1 in the cell to a control, wherein the control is a known level of Mcl-1 characteristic of a non-cancer cell, a level of Mcl-1 in a non-cancerous cell of the subject, or a level of Mcl-1 in a cancer cell of the subject at a different point in time. In some embodiments, the monitoring comprises an assay that is an ELISA, a competitive ELISA, surface plasmon resonance analysis, in vitro neutralization assay, in vivo neutralization assay, an immunohistochemical assay with FACS sorting, or an immunohistochemical assay without FACS sorting. In some embodiments, the cancer cell is a leukemia cell, a lymphoma cell, or a myeloma cell. In some embodiments, the cancer treatment comprises administration of AMG 176 of formula I:

I

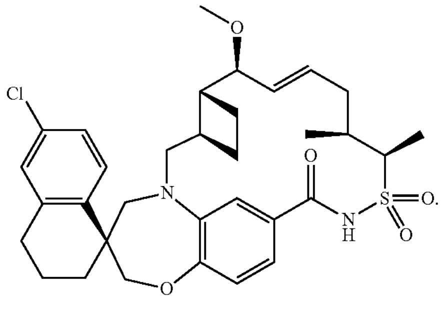

In some embodiments, the cancer treatment comprises administration of AMG 397 of formula II:

II

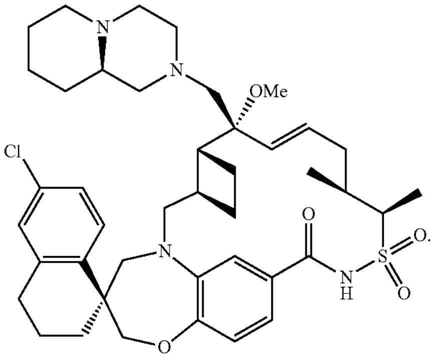

In some embodiments, the cancer cell is a myeloid leukemia cell. In some embodiments, the cancer cell is an organ cancer cell. In some embodiments, the antibody or fragment thereof is a monoclonal antibody or fragment thereof comprising the light chain complementarity determining region 1 (LCDR1) of SEQ ID NO:4, the light chain complementarity determining region 2 (LCDR2) of SEQ ID NO:5, the light chain complementarity determining region 3 (LCDR3) of SEQ ID NO:6, the heavy chain complementarity determining region 1 (HCDR1) of SEQ ID NO:16, the heavy chain complementarity determining region 2 (HCDR2) of SEQ ID NO:17, and the heavy chain complementarity determining region 3 (HCDR3) of SEQ ID NO:18, or the antibody or fragment thereof is a monoclonal antibody or fragment thereof comprising the LCDR1 of SEQ ID NO:10, the LCDR2 of SEQ ID NO:11, the LCDR3 of SEQ ID NO:12, the HCDR1 of SEQ ID NO:22, the HCDR2 of SEQ ID NO:23, and the HCDR3 of SEQ ID NO:24. In some embodiments, the antibody or fragment thereof comprises the light chain variable region sequence of SEQ ID NO:27, the heavy chain variable region sequence of SEQ ID NO:28, or the light chain variable region of SEQ ID NO:31 and the heavy chain variable region of SEQ ID NO:32. In some embodiments, the antibody or fragment thereof is in the form of a single-chain antibody, a single-chain variable fragment (scFv), a scFv, a Fab, a F(ab')2, a bispecific antibody, a trispecific antibody, a single chain variable fragment (scFv), a disulfide-bond-stabilized single chain variable fragment (ds-scFv), a single domain antibody (sdAb), a single chain Fab fragment (scFab), a diabody, a triabody, a tetrabody, a minibody, a Fab, a $F(ab')_2$, a VHH/VH fragment, a peptibody, a chimeric antigen receptor (CAR), or a bispecific T-cell engager (BiTE).

Still another aspect of the disclosure is a method of treating cancer in a subject comprising administering a therapeutically effective amount of the anti-Mcl-1 antibody or fragment thereof disclosed herein to the subject. In some embodiments, the cancer cell is a leukemia cell, a lymphoma cell, or a myeloma cell. In some embodiments, the cancer cell is a myeloid leukemia cell. In some embodiments, the cancer cell is an organ cancer cell. In some embodiments, the antibody or fragment thereof is a monoclonal antibody or fragment thereof comprising the light chain complementarity determining region 1 (LCDR1) of SEQ ID NO:4, the light chain complementarity determining region 2 (LCDR2) of SEQ ID NO:5, the light chain complementarity determining region 3 (LCDR3) of SEQ ID NO:6, the heavy chain complementarity determining region 1 (HCDR1) of SEQ ID NO:16, the heavy chain complementarity determining region 2 (HCDR2) of SEQ ID NO:17, and the heavy chain complementarity determining region 3 (HCDR3) of SEQ ID NO:18, or the antibody or fragment thereof is a monoclonal antibody or fragment thereof comprising the LCDR1 of SEQ ID NO:10, the LCDR2 of SEQ ID NO:11, the LCDR3 of SEQ ID NO:12, the HCDR1 of SEQ ID NO:22, the HCDR2 of SEQ ID NO:23, and the HCDR3 of SEQ ID NO:24. In some embodiments, the antibody or fragment thereof comprises the light chain variable region sequence of SEQ ID NO:27, the heavy chain variable region sequence of SEQ ID NO:28, or the light chain variable region of SEQ ID NO:31 and the heavy chain variable region of SEQ ID NO:32. In some embodiments, the antibody or fragment thereof is in the form of a single-chain antibody, a single-chain variable fragment (scFv), a scFv, a Fab, a F(ab')2, a bispecific antibody, a trispecific antibody, a single chain variable fragment (scFv), a disulfide-bond-stabilized single chain variable fragment (ds-scFv), a single domain antibody (sdAb), a single chain Fab fragment (scFab), a diabody, a triabody, a tetrabody, a minibody, a Fab, a $F(ab')_2$, a VHH/VH fragment, a peptibody, a chimeric antigen receptor (CAR), or a bispecific T-cell engager (BiTE).

Other features and advantages of the disclosure will become apparent from the following detailed description, including the drawing. It should be understood, however, that the detailed description and the specific examples, while indicating preferred embodiments, are provided for illustration only, because various changes and modifications within the spirit and scope of the invention will become apparent to those skilled in the art from the detailed description.

DETAILED DESCRIPTION

Figure 1:
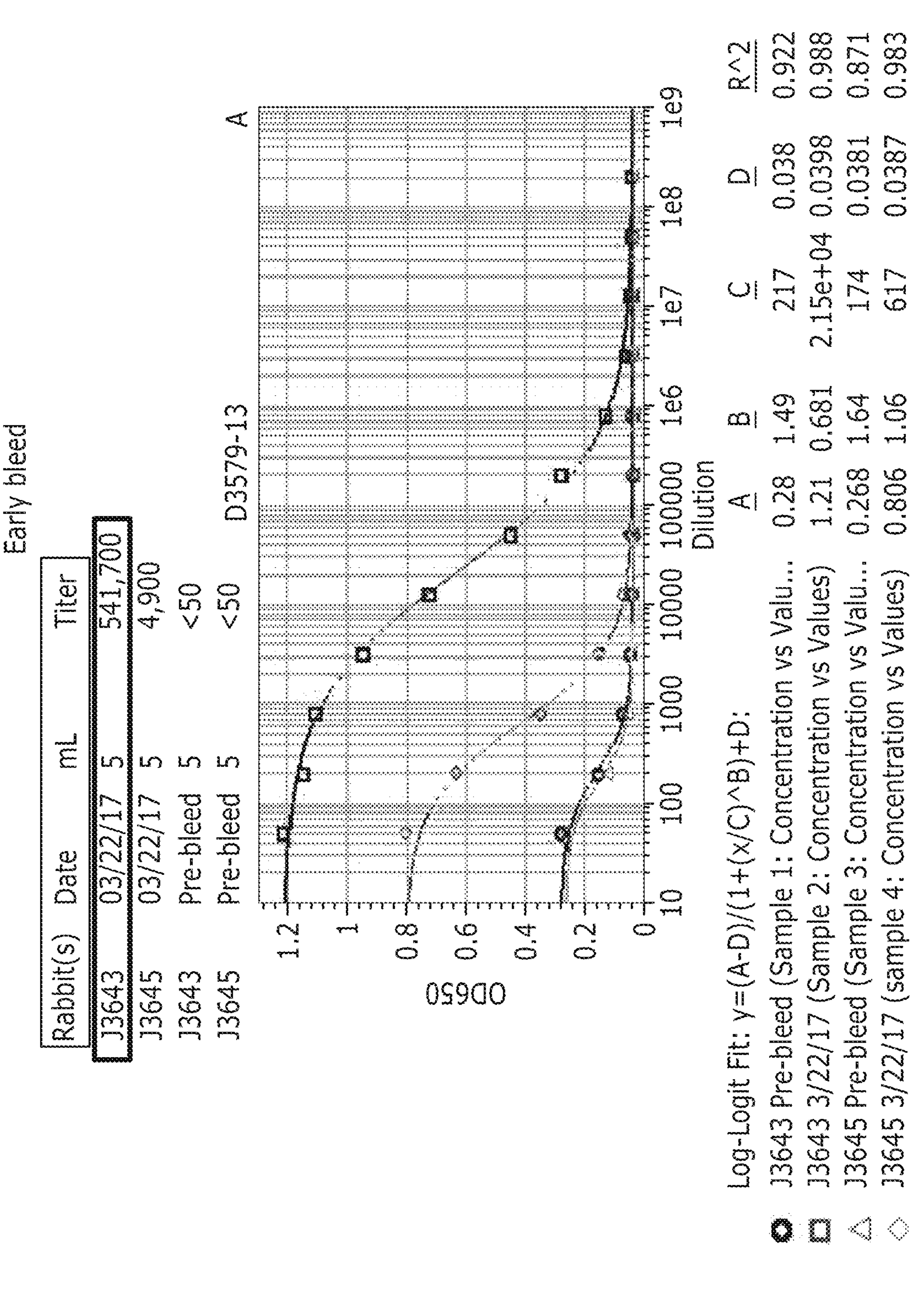
FIG. 1. Rabbit antibody immune response to Mcl-1 immunogen. ELISA assays were run by serially diluting rabbit sera on 384-well plates coated with biotin-labeled Mcl-1 protein. Sample absorbance values yielded the curves shown. A) Mcl-1 immune response from an early bleed of rabbit J3643. B) Mcl-1 immune response obtained from a late bleed of rabbit J3643.
Figure 1:
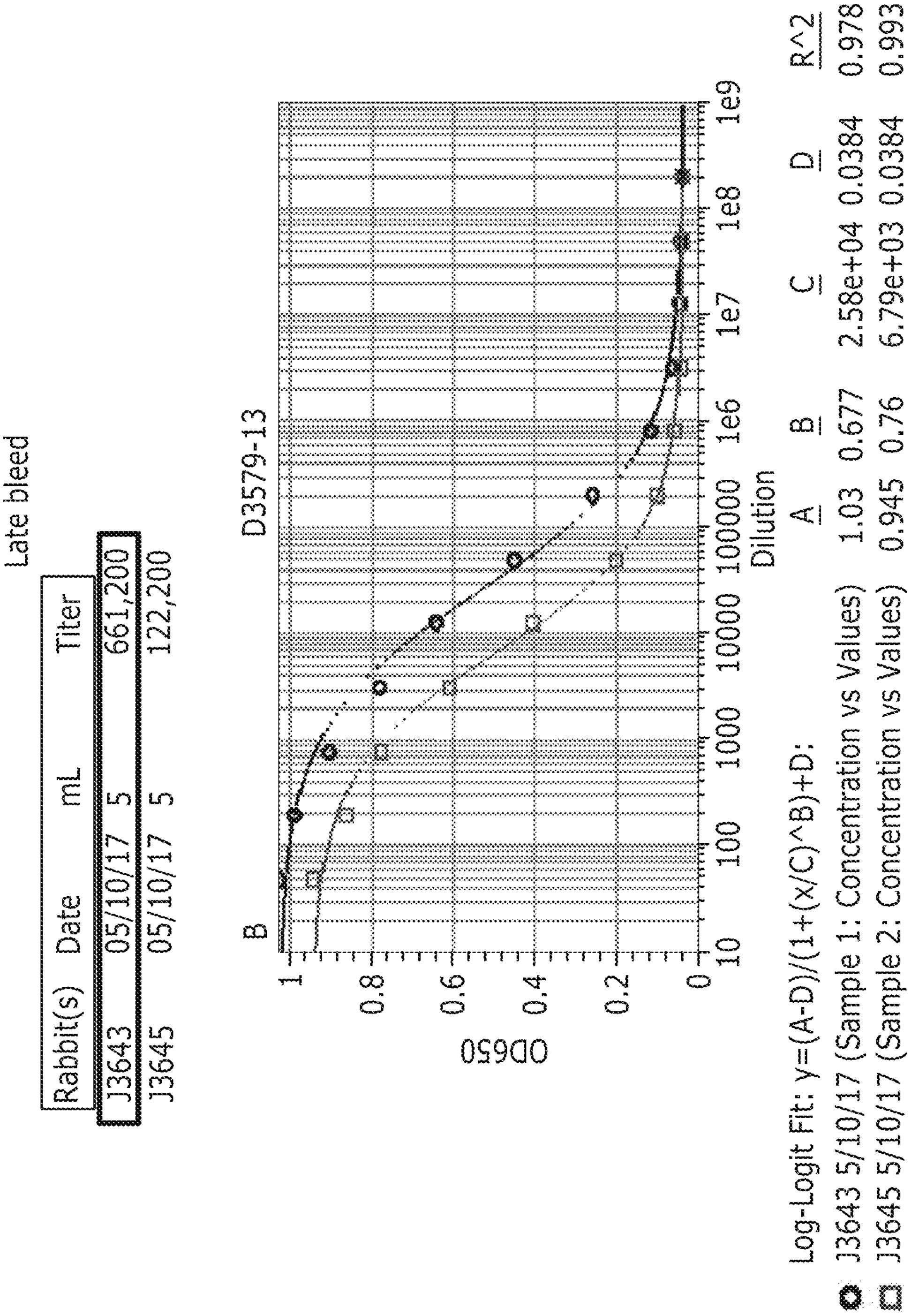
Figure 2:
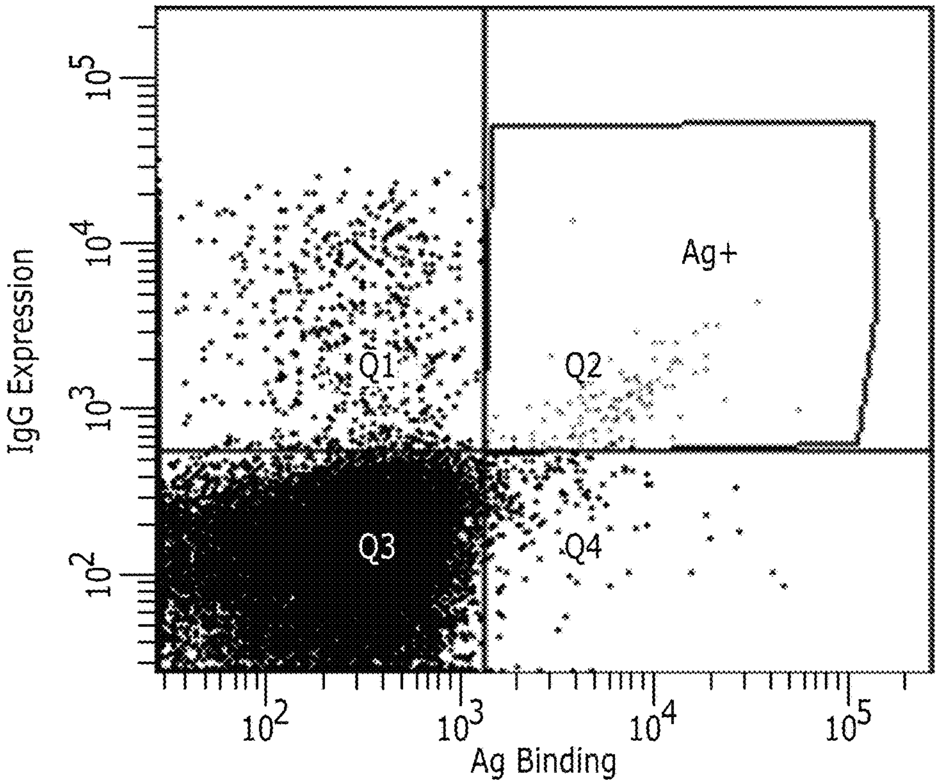
FIG. 2. FACS sorting of rabbit B-cells into clonal culture plates on full-length Mcl-1 to enable recombinant rescue of rabbit monoclonal antibodies.
Figure 3:
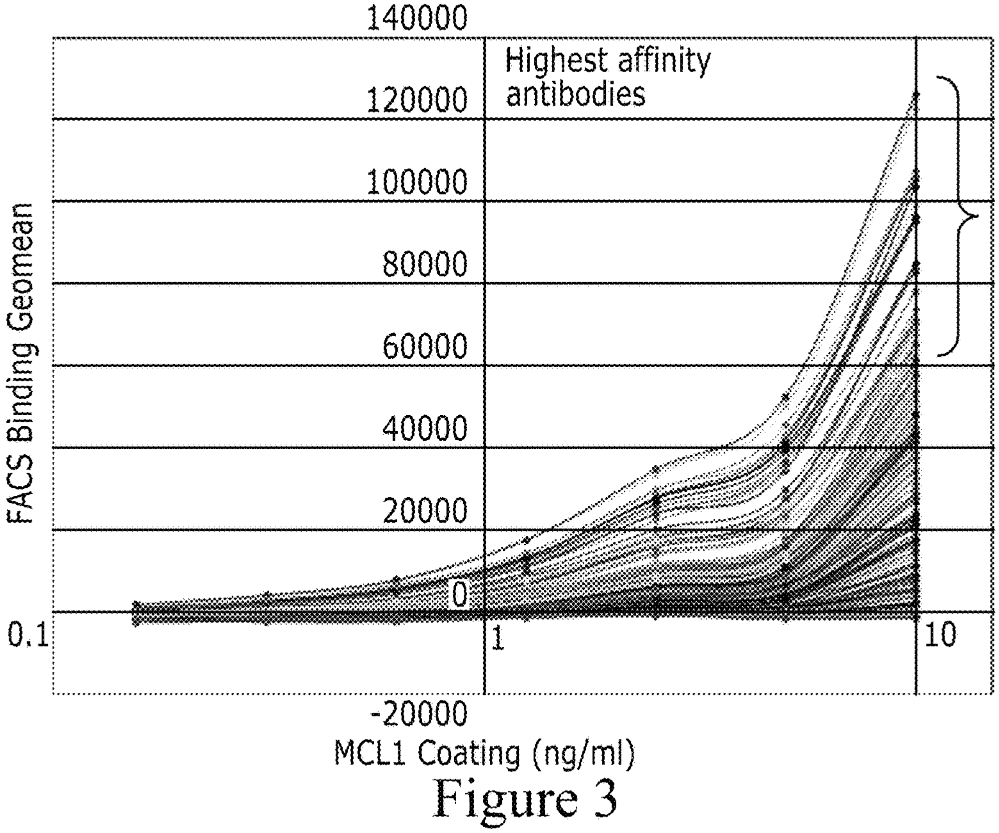
FIG. 3. The results of a limited antigen binding screen are presented, which led to a panel of antibodies ranked by relative affinities to Mcl-1. Bead multiplex at different antigen coating concentrations. An 18-hour incubation was used to achieve equilibrium.

Described herein are the immunization regimen, B cell screening efforts, and recombinant antibody rescue efforts that led to discovery of specific anti-Mcl-1 antibodies. The antibodies resulting from this effort demonstrate surprisingly superior binding affinity and specificity compared to antibodies known in the art, which provided the basis for developing screening assays to monitor Mcl-1 levels in vitro and in vivo, for example as a monitor of cancer treatment.

Conventional techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to methods well known in the art and as described in various general and more specific references that are cited and discussed throughout the present specification. See, e.g., Sambrook et al., 2001, Molecular Cloning: A Laboratory Manual, 3d ed., Cold Spring Harbor Laboratory Press, Cold Spring Harbor, N.Y., which is incorporated herein by reference for any purpose.

Unless specific definitions are provided, the nomenclature utilized in connection with, and the laboratory procedures and techniques of, analytical chemistry, synthetic organic chemistry, and medicinal and pharmaceutical chemistry described herein are those well known and commonly used in the art. Similarly, conventional techniques may be used for chemical syntheses, chemical analyses, pharmaceutical preparation, formulation, and delivery, and treatment of patients.

As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise. For the terms "for example" and "such as" and grammatical equivalences thereof, the phrase "and without limitation" is understood to follow unless explicitly stated otherwise.

The phrases "biological property", "biological characteristic", and the term "activity", in reference to an antibody of the present disclosure are used interchangeably herein and include, but are not limited to, epitope affinity and specificity (e.g., anti-human Mcl-1 human antibody binding to human Mcl-1), ability to antagonize the activity of the targeted polypeptide (e.g., Mcl-1 activity), the in vivo stability of the antibody, and the immunogenic properties of the antibody. Other identifiable biological properties or characteristics of an antibody recognized in the art include, for example, cross-reactivity, (i.e., with non-human homologs of Mcl-1, or with other proteins or tissues, generally), and ability to preserve high expression levels of protein in mammalian cells. The aforementioned properties or characteristics can be observed or measured using art-recognized techniques including, but not limited to, ELISA, competitive ELISA, surface plasmon resonance analysis, in vitro and in vivo neutralization assays, and immunohistochemistry with tissue sections from different sources including human, primate, or any other appropriate source. Particular activities and biological properties of anti-human Mcl-1 human antibodies are described in further detail in the Examples below.

The term "biological sample", as used herein, includes, but is not limited to, any quantity of a substance from a living thing or formerly living thing. Such living things include, but are not limited to, humans, mice, monkeys, rats, rabbits, horses, cattle, sheep, goats, and other animals. Such substances include, but are not limited to, blood, serum, urine, cells, organs, tissues, bone, bone marrow, lymph nodes, and skin.

As used herein, the terms "label" or "labeled" refers to incorporation of a detectable marker, e.g., by incorporation of a radiolabeled amino acid or attachment to a polypeptide of biotin moieties that can be detected by labeled avidin (e.g., streptavidin comprising a detectable marker such as a fluorescent marker, a chemiluminescent marker or an enzymatic activity that can be detected by optical or colorimetric methods). In certain embodiments, the label can also be therapeutic. Various methods of labeling polypeptides and glycoproteins are known in the art and may be used advantageously in the methods disclosed herein. Examples of labels for polypeptides include, but are not limited to, radioisotopes or radionuclides such as $^{3}H$, $^{14}C$, $^{15}N$, $^{35}S$, $^{90}U$, $^{99}mTc$, $^{111}In$, $^{125}I$, and $^{131}I$, fluorescent labels (e.g., fluorescein isothiocyanate or FITC, rhodamine, or lanthanide phosphors), enzymatic labels (e.g., horseradish peroxidase, β-galactosidase, luciferase, alkaline phosphatase), chemiluminescent labels, hapten labels such as biotinyl groups, and predetermined polypeptide epitopes recognized by a secondary reporter (e.g., leucine zipper pair sequences, binding sites for secondary antibodies, metal binding domains, or epitope tags). In certain embodiments, labels are attached by spacer arms (such as $(CH_2)_n$, where n is less than about 20) of various lengths to reduce potential steric hindrance.

The term "naturally occurring" or "native" as used herein and as applied to an object refers to the fact that the object can be found in nature. For example, a polypeptide or polynucleotide sequence that is present in an organism (including viruses) that can be isolated from a source in nature and that has not been intentionally modified by man is naturally occurring. The term "non-naturally occurring" or "non-native" as used herein refers to a material that is not found in nature or that has been structurally modified or synthesized by man. For example, "non-naturally occurring" can refer to a variant, such as a polynucleotide variant that can be produced using art-known mutagenesis techniques, or a polypeptide variant produced by such a polynucleotide variant. Such variants include, for example, those produced by nucleotide substitutions, deletions or additions that may involve one or more nucleotides. Polynucleotide variants can be altered in coding or non-coding regions or both.

Alterations in the coding regions may produce conservative or non-conservative amino acid substitutions, deletions, or additions. Especially certain among these are silent substitutions, additions, deletions, and conservative substitutions, which do not alter the properties and activities of an anti-Mcl-1 antibody. One of skill in the art can readily determine how to generate such a variant using methods well known in the art. The term "naturally occurring nucleotides" includes deoxyribonucleotides and ribonucleotides. The term "modified nucleotides" includes nucleotides with modified or substituted sugar groups and the like. The term "oligonucleotide linkages" includes phosphorothioate, phosphorodithioate, phosphoroselenoate, phosphorodiselenoate, phosphoroanilothioate, phoshoraniladate, and phosphoroamidate linkages, and the like. See, e.g., LaPlanche et al., Nucl Acids Res., 14:9081 (1986); Stec et al., J Am. Chem. Soc., 106: 6077 (1984); Stein et al., Nucl. Acid. Res., 16:3209 (1988); Zon et al., Anti-Cancer Drug Design, 6:539 (1991); Zon et al., OLIGONUCLEOTIDES AND ANALOGUES: A PRACTICAL APPROACH, pp. 87-108 (F. Eckstein, Ed.; 1991), Oxford University Press, Oxford England; Stec et al., U.S. Pat. No. 5,151,510; Uhlmann et al., Chemical Reviews, 90:543 (1990), the disclosures of which are hereby incorporated by reference for any purpose. An oligonucleotide can include a detectable label to enable detection of the oligonucleotide or hybridization thereof.

The term "isolated protein" means that a subject protein (1) is free of at least some other proteins with which it would be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of synthetic origin, or any combination thereof. In one embodiment, the isolated protein is substantially free from proteins or polypeptides or other contaminants that are found in its natural environment that would interfere with its use.

The terms "polypeptide" or "protein" means molecules having the sequence of native proteins, that is, proteins produced by naturally occurring and specifically non-recombinant cells, or genetically engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass anti-Mcl-1 antibodies, or sequences that have deletions from, additions to, and/or substitutions of one or more amino acid of an anti-Mcl-1 antibody.

The term "polypeptide fragment" refers to a polypeptide that has an amino-terminal deletion, a carboxyl-terminal deletion, and/or an internal deletion. In certain embodiments, fragments are at least 5 to about 500 amino acids long. It will be appreciated that in certain embodiments, fragments are at least 5, 6, 8, 10, 14, 20, 50, 70, 100, 110, 150, 200, 250, 300, 350, 400, or 450 amino acids long. Particularly useful polypeptide fragments include functional domains, including binding domains, particularly antigen-binding domains, especially wherein the antigen is an epitope of human Mcl-1. In the case of an anti-Mcl-1 antibody, useful fragments include but are not limited to a CDR region, a variable domain of a heavy or light chain, a portion of an antibody chain or just its variable region including two CDRs, and the like.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

An "antigen binding protein" is a protein that binds specifically to an antigen. Exemplary antigen binding proteins include any form of antibody or antigen-binding fragment thereof.

The term "epitope" includes any site on an antigen that is capable of specific binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. In certain embodiments, an antibody is said to specifically bind an antigen when the equilibrium dissociation constant is about $10^{-6}$ M, $10^{-7}$ M, $10^{-8}$ M, $10^{-9}$ M, $10^{-10}$ M, $10^{-11}$ M, $10^{-12}$ M, or less than about $10^{-12}$ M.

An antibody binds "essentially the same epitope" as a reference antibody, when the two antibodies recognize identical or sterically overlapping epitopes. The most widely used and rapid methods for determining whether two antibodies bind to identical or sterically overlapping epitopes are competition assays, which can be configured in a number of different formats, using either labeled antigen or labeled antibody. Usually, the antigen is immobilized on a substrate, and the ability of unlabeled antibodies to block the binding of labeled antibodies is measured using radioactive isotopes or enzyme labels.

In assessing antibody binding and specificity according to the invention, an antibody substantially inhibits adhesion of a ligand to a receptor when an excess of antibody reduces the quantity of ligand bound to receptor by at least about 20%, 40%, 60%, 80%, 85%, or more (as measured, for example, using an in vitro competitive binding assay).

"Antibody" or "antibody peptide(s)" refer to an intact antibody, or a binding fragment thereof that competes with the intact antibody for specific binding. In certain embodiments, binding fragments are produced by recombinant DNA techniques. In additional embodiments, binding fragments are produced by enzymatic or chemical cleavage of intact antibodies. Binding fragments include, but are not limited to, F(ab), F(ab'), $F(ab')_2$, Fv, and single-chain antibodies.

An "isolated" antibody is one that has been identified and separated and/or recovered from a component of its natural environment. Contaminant components of its natural environment are materials that would interfere with use of an antibody in an assay, diagnosis, or therapy, and may include enzymes, hormones, and other proteinaceous or non-proteinaceous substances. In certain embodiments, the antibody is purified (1) to greater than 95% or greater than 99% by weight of antibody as determined by the Lowry method, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells because at least one component of the antibody's natural environment is not present.

A "neutralizing antibody" is an antibody molecule that is able to block or substantially reduce an effector function of a target antigen to which it binds. Accordingly, a "neutralizing" anti-Mcl-1 antibody is capable of blocking or substantially reducing an effector function of Mcl-1. "Substantially reduce" is intended to mean at least about 60%, at least about 70%, at least about 75%, at least about 80%, at least about 85%, or at least about 90% reduction of an effector function of the target antigen (e.g., human Mcl-1).

The term "specific binding agent" refers to a naturally occurring or non-naturally occurring molecule that specifically binds to a target. Examples of specific binding agents include, but are not limited to, proteins, peptides, nucleic acids, carbohydrates, and lipids. In certain embodiments, a specific binding agent is an antibody.

The term "specific binding agent to Mcl-1" refers to a specific binding agent that specifically binds any portion of Mcl-1. In certain embodiments, a specific binding agent to Mcl-1 is an antibody that binds specifically to Mcl-1.

By way of example, an antibody "binds specifically" to a target if the antibody, when labeled, can be competed away from its target by the corresponding non-labeled antibody.

The term "immunologically functional immunoglobulin fragment" as used herein refers to a polypeptide fragment that contains at least the CDRs of the immunoglobulin heavy and light chains. An immunologically functional immunoglobulin fragment of the disclosure is capable of binding to an antigen. In certain embodiments, the antigen is a ligand that specifically binds to a receptor. In these embodiments, binding of an immunologically functional immunoglobulin fragment of the disclosure prevents binding of the ligand to its receptor, interrupting the biological response resulting from ligand binding to the receptor. In one embodiment, an immunologically functional immunoglobulin fragment of the disclosure binds specifically to Mcl-1. Preferably, the fragment binds specifically to human Mcl-1.

The term "operably linked" means that the components to which the term is applied are in a relationship that allows them to carry out their inherent functions under suitable conditions, or to operate as expected or intended. For example, a control sequence "operably linked" to a protein coding sequence is ligated thereto so that expression of the protein coding sequence is controlled, at least in part, by the control sequence, which typically results in expression of the coding sequence under conditions compatible with the transcriptional activity of the control sequence(s).

The term "pharmaceutical agent", "agent", or "drug" refers to a chemical compound, a mixture of chemical compounds, a biological macromolecule, or an extract made from biological materials capable of inducing a desired therapeutic effect when properly administered to a subject, e.g., a patient. The expression "pharmaceutically effective amount" in reference to a pharmaceutical composition comprising one or a plurality of the antibodies disclosed herein is understood to mean an amount of the said pharmaceutical composition that is capable of abolishing, in a subject such as a patient, the decrease in the sensitivity threshold to external stimuli with a return of this sensitivity threshold to a level comparable to that observed in healthy subjects.

The term "excipient", as used herein, means any pharmaceutically acceptable additive, carrier, diluent, adjuvant or other ingredient, other than the active pharmaceutical ingredient (API), which is typically included for formulation and/or administration to a patient. Handbook of Pharmaceutical Excipients, 5th Edition, Rowe, et al., eds., Pharmaceutical Press, 2005, Hardback, 928, 0853696187.

The term "polynucleotide" as used herein means single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. The modifications include base modifications, such as bromuridine, ribose modifications, such as arabinoside and 2',3'-dideoxyribose, and internucleotide linkage modifications, such as phosphorothioate, phosphorodithioate, phosphoroselenoate, phosphorodiselenoate, phosphoroanilothioate, phoshoraniladate and phosphoroamidate. The term "polynucleotide" specifically includes single- and double-stranded forms of DNA or RNA.

The term "oligonucleotide" as used herein includes naturally occurring and modified nucleotides linked together by naturally occurring and/or non-naturally occurring oligonucleotide linkages. Oligonucleotides are a polynucleotide subset comprising members that are generally single-stranded and have a length of 200 nucleotides or fewer. In certain embodiments, oligonucleotides are 10 to 60 nucleotides in length. In certain embodiments, oligonucleotides are 12, 13, 14, 15, 16, 17, 18, 19, or 20 to 40 nucleotides in length. Oligonucleotides may be single-stranded or double-stranded, e.g., for use in the construction of a genetic mutant. Oligonucleotides of the disclosure may be sense or antisense oligonucleotides with reference to a protein-coding sequence.

The term "control sequence" as used herein refers to a polynucleotide sequence that can affect expression, processing, and/or intracellular localization of coding sequences to which they are operably linked. The nature of such control sequences may depend upon the host organism. In particular embodiments, control sequences for prokaryotes may include a promoter, ribosomal binding site, and transcription termination sequence. In other particular embodiments, control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "vector" includes a nucleic acid molecule capable of carrying into a cell another nucleic acid to which it has been linked. One type of vector is a "plasmid", which refers to a circular double stranded DNA loop into which additional DNA segments may be ligated. Another type of vector is a viral vector, wherein additional DNA segments may be ligated into a viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors useful in the practice of recombinant DNA techniques are often plasmids. In the present specification, "plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, are also contemplated by the disclosure.

The phrase "recombinant host cell" (or simply "host cell") includes a cell into which a recombinant expression vector has been introduced. It will be understood by those of skill in the art that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A wide variety of host expression systems can be used to express the antibodies of the disclosure including bacterial, yeast, baculoviral and mammalian expression systems (as well as phage display expression systems). An example of a suitable bacterial expression vector is pUC19. To express an antibody recombinantly, a host cell is transfected with one or more recombinant expression vectors carrying DNA fragments encoding the immunoglobulin light and heavy chains of the antibody such that the light and heavy chains are expressed in the host cell and can be secreted into the medium in which the host cells are cultured, resulting in conditioned medium. Antibodies can be recovered from conditioned medium using techniques well known in the art. Standard recombinant DNA methodologies are used to obtain antibody heavy and light chain genes, incorporate these genes into recombinant expression vectors, and introduce the vectors into host cells, such as those described in Sambrook et al., 2001, MOLECULAR CLONING, A LABORATORY MANUAL, Cold Spring Harbor Laboratories, Ausubel, F. M. et al., (eds.), CURRENT PROTOCOLS IN MOLECULAR BIOLOGY, Greene Publishing Associates, (1989) and in U.S. Pat. No. 4,816,397.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52-456; Sambrook et al., 2001, MOLECULAR CLONING, A LABORATORY MANUAL, Cold Spring Harbor Laboratories; Davis et at, 1986, BASIC METHODS IN MOLECULAR BIOLOGY, Elsevier; and Chu et al., 1981, Gene 13: 197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with DNA from the cell by physically integrating into a chromosome of the cell, or may be maintained transiently as an episomal element without being replicated, or may replicate independently as a plasmid. A cell is considered to have been stably transformed when the DNA is replicated with the division of the cell.

All compounds, and pharmaceutically acceptable salts thereof, can be found together with other substances such as water and solvents (e.g., hydrates and solvates).

Antigen Binding Proteins

Provided herein are antigen-binding proteins that bind to Mcl-1. In various embodiments, the antigen binding proteins bind to isoform 1 of Mcl-1, which inhibits apoptosis and thereby enhances cell survival. The antigen-binding proteins of the disclosure can take any one of many forms of antigen-binding proteins known in the art. In various embodiments, the antigen-binding proteins of the disclosure take the form of an antibody, an antigen-binding antibody fragment, an antibody protein product, or an antibody derivative.

In various embodiments, the antigen-binding protein comprises, consists essentially of, or consists of an antibody. As used herein, the term "antibody" refers to a protein having a conventional immunoglobulin format, comprising heavy and light chains, and comprising variable and constant regions. For example, an antibody may be an IgG which is a "Y-shaped" structure of two identical pairs of polypeptide chains, each pair having one "light" chain (typically having a molecular weight of about 25 kDa) and one "heavy" chain (typically having a molecular weight of about 50-70 kDa). An antibody has a variable region and a constant region. In IgG formats, the variable region is generally about 100-110 or more amino acids in length, comprising three complementarity determining regions (CDRs), which are primarily responsible for antigen recognition, and substantially varies among other antibodies that bind to different antigens. The constant region allows the antibody to recruit cells and molecules of the immune system. The variable region is found at the N-terminal regions of each naturally occurring light chain and heavy chain, while the constant region is made of the C-terminal portions of naturally occurring heavy and light chains. (Janeway et al., "Structure of the Antibody Molecule and the Immunoglobulin Genes", Immunobiology: The Immune System in Health and Disease, $4^{th}$ ed. Elsevier Science Ltd./Garland Publishing, (1999)).

The general structure and properties of CDRs of antibodies are well known. Briefly, in an antibody scaffold, the CDRs are embedded within a framework in the heavy and light chain variable regions where they constitute the regions largely responsible for antigen binding and recognition. A variable region typically comprises at least three heavy or light chain CDRs (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk, 1987). In a related embodiment, the residues of the framework are altered. The heavy chain framework regions which can be altered lie within regions designated H-FR1, H-FR2, H-FR3 and H-FR4, which surround the heavy chain CDR residues, and the residues of the light chain framework regions which can be altered lie within the regions designated L-FR1, L-FR2, L-FR3 and L-FR4, which surround the light chain CDR residues. An amino acid within the framework region may be replaced, for example, with any suitable amino acid identified in a human framework or human consensus framework.

Antibodies can comprise any constant region known in the art. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the present disclosure include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in various embodiments, the antibody is an antibody of isotype IgA, IgD, IgE, IgM, or IgG, including any one of IgG1, IgG2, IgG3 or IgG4. In various aspects, the antibody comprises a constant region comprising one or more amino acid modifications, relative to the naturally occurring counterpart, in order to improve half-life/stability or to render the antibody more suitable for expression/commercial production. In various instances, the antibody comprises a constant region wherein the C-terminal Lys residue that is present in the naturally occurring counterpart is removed or clipped.

The antibody can be a monoclonal antibody. In some embodiments, the antibody comprises a sequence that is substantially similar to a naturally occurring antibody produced by a mammal, e.g., mouse, rabbit, goat, horse, chicken, hamster, human, and the like. In this regard, the antibody can be considered as a mammalian antibody, e.g., a mouse antibody, rabbit antibody, goat antibody, horse antibody, chicken antibody, hamster antibody, human antibody, and the like. In certain aspects, the antigen-binding protein is an antibody, such as a human antibody. In certain aspects, the antigen-binding protein is a chimeric antibody or a humanized antibody. The term "chimeric antibody" refers to an antibody containing domains from two or more different antibodies. A chimeric antibody can, for example, contain the constant domains from one species and the variable domains from a second species, or more generally, can contain stretches of amino acid sequence from at least two species. A chimeric antibody also can contain domains of two or more different antibodies within the same species. The term "humanized" when used in relation to antibodies refers to antibodies having regions engineered to more closely resemble human antibody regions, thereby reducing the immunogenicity of the humanized form of the antibody. Typically, engineering is focused on regions other than the CDRs, such as framework regions and constant regions of antibodies. This engineering reduces immunogenicity while retaining the binding characteristics of the original non-human antibody. For example, humanizing can involve grafting a CDR from a non-human antibody, such as a mouse antibody, into a human antibody. Humanizing also can involve select amino acid substitutions to make a non-human sequence more similar to a human sequence. Information, including sequence information for human antibody heavy and light chain constant regions, is publicly available through the Uniprot database as well as other databases well-known to those in the field of antibody engineering and production. For example, the IgG2 constant region is available from the Uniprot database as Uniprot number P01859, incorporated herein by reference.

An antibody can be cleaved into fragments by enzymes, such as papain and pepsin. Papain cleaves an antibody to produce two Fab fragments and a single Fc fragment. Pepsin cleaves an antibody to produce a $F(ab')_2$ fragment and a pFc' fragment. In various aspects of the disclosure, the antigen-binding protein is an antigen-binding fragment of an antibody (i.e., an antigen-binding antibody fragment, antigen-binding fragment, or antigen-binding portion). In various instances, the antigen-binding antibody fragment is a Fab fragment or a $F(ab')_2$ fragment.

The architecture of antibodies has been exploited to create a growing range of alternative antibody formats that spans a molecular-weight range of at least about 12-150 kDa and has a valency (n) range from monomeric (n=1), to dimeric (n=2), to trimeric (n=3), to tetrameric (n=4), and potentially higher; such alternative antibody formats are referred to herein as "antibody protein products". Antibody protein products include those based on the full antibody structure and those that mimic antibody fragments that retain full antigen-binding capacity, e.g., scFvs, Fabs and VHH/VH. A relatively small antigen-binding fragment that retains the complete antigen binding site of the cognate antibody is an Fv fragment, which consists entirely of variable (V) regions. A soluble, flexible amino acid peptide linker is used to connect the VL and VH regions in forming a scFv (single-chain fragment variable, or more commonly, a single-chain variable fragment) for stabilization of the molecule, or the constant (C) domains are added to the V regions to generate a Fab fragment (fragment, antigen-binding). Both scFv and Fab fragments can be easily produced in host cells, e.g., prokaryotic host cells. Other antibody protein products include disulfide-bond stabilized scFv (ds-scFv), single chain Fab (scFab), as well as di- and multimeric antibody formats like dia-, tria- and tetra-bodies, or minibodies (mini-Abs) that comprise different formats consisting of scFvs linked to oligomerization domains. The smallest fragments are VHH/VH regions of camelid heavy chain antibodies as well as single domain antibodies (sdAb). The building block that is most frequently used to create novel antibody formats is the single-chain variable (V)-domain antibody fragment (scFv), which comprises V domains from the heavy and light chain (VH and VL domains) linked by a peptide linker of about 15 amino acid residues. A peptibody or peptide-Fc fusion is yet another antibody protein product. The structure of a peptibody consists of a biologically active peptide grafted onto an Fc domain. Peptibodies are known in the art. Other forms of antigen-binding proteins of the disclosure that are fusion proteins include chimeric antigen receptors (CARs) and bispecific T-cell engagers (BiTES).

Still other antibody protein products according to the disclosure include a single-chain antibody (SCA); the above-noted diabody; triabody; and tetrabody; bispecific or trispecific antibodies, and the like. Bispecific antibodies can be divided into several major classes: BsIgG, appended IgG, bispecific antibody (BsAb) fragments, bispecific fusion proteins, and BsAb conjugates. See, e.g., Spiess et al., Molecular Immunology 67(2) Part A: 97-106 (2015).

In various aspects, the antigen-binding protein of the disclosure comprises, consists essentially of, or consists of any one of these antibody protein products. In various aspects, the antigen-binding protein comprises, consists essentially of, or consists of any one of an scFv, Fab VHH/VH, Fv fragment, ds-scFv, scFab, dimeric antibody, multimeric antibody (e.g., a diabody, triabody, tetrabody), miniAb, peptibody VHH/VH of camelid heavy chain antibody, sdAb, a bispecific or trispecific antibody, BsIgG, appended IgG, BsAb fragment, bispecific fusion protein, or a BsAb conjugate.

In various instances, the antigen-binding protein of the disclosure is an antibody protein product in monomeric form, or polymeric (e.g., oligomeric or multimeric) form. In certain embodiments in which the antibody comprises two or more distinct antigen binding region fragments, the antibody is considered bispecific, trispecific, or multi-specific, or bivalent, trivalent, or multivalent, depending on the number of distinct epitopes that are recognized and bound by the antibody. A bivalent antibody other than a "multi-specific" or "multifunctional" antibody, in certain embodiments, is understood to comprise binding sites having identical antigenic specificity.

In various embodiments, an anti-Mcl-1 antibody or antibody variant thereof is selected from the group consisting of a human antibody, a humanized antibody, a chimeric antibody, a monoclonal antibody, a recombinant antibody, an antigen-binding antibody fragment, a single chain antibody, a monomeric antibody, a diabody, a triabody, a tetrabody, a Fab fragment, a $F(ab')_2$ fragment, a scFab fragment, an IgG1 antibody, an IgG2 antibody, an IgG3 antibody, and an IgG4 antibody.

In various aspects, the antigen-binding protein of the disclosure is linked to a therapeutic agent. The therapeutic agent may be any therapeutic known in the art including, but not limited to, chemotherapeutic agents, cytokines and growth factors, cytotoxic agents, and the like.

Affinity and Avidity

The antigen-binding proteins provided herein bind to Mcl-1 in a non-covalent and reversible manner. In various embodiments, the binding strength of the antigen-binding protein to Mcl-1 may be described in terms of its affinity, a measure of the strength of interaction between the binding site of the antigen-binding protein and the Mcl-1 epitope. In various aspects, the antigen-binding proteins provided herein have high-affinity for Mcl-1 and thus will bind a greater amount of Mcl-1 in a shorter period of time than low-affinity antigen-binding proteins. In various aspects, the antigen-binding protein has an equilibrium association constant, $K_A$, which is at least $10^5$ $mol^{-1}$, at least $10^6$ $mol^{-1}$, at least $10^7$ $mol^{-1}$, at least $10^8$ $mol^{-1}$, at least $10^9$ $mol^{-1}$, or at least $10^{10}$ $mol^{-1}$ or at least $10^{10}$ $mol^{-1}$ least $10^{10}$ $mol^{-1}$. As understood by the artisan of ordinary skill, $K_A$ can be influenced by factors including pH, temperature and buffer composition.

In various embodiments, the binding strength of the antigen-binding protein to Mcl-1 may be described in terms of its sensitivity. $K_D$ is the equilibrium dissociation constant, a ratio of $k_{off}/k_{on}$, between the antigen-binding protein and Mcl-1. $K_D$ and $K_A$ are inversely related. The $K_D$ value relates to the concentration of the antigen-binding protein (the amount of antigen-binding protein needed for a particular experiment) and so the lower the $K_D$ value (lower concentration) the higher the affinity of the antigen-binding protein. In various aspects, the binding strength of the antigen-binding protein to Mcl-1 may be described in terms of $K_D$. In various aspects, the $K_D$ of the antigen-binding proteins provided herein is about $10^{-1}$, about $10^{-2}$, about $10^{-3}$, about $10^{-4}$, about $10^{-8}$, about $10^{-8}$, or less. In various aspects, the $K_D$ of the antigen-binding proteins provided herein is micromolar, nanomolar, picomolar or femtomolar. In various aspects, the $K_D$ of the antigen-binding proteins provided herein is within a range of about $10^{-4}$ to $10^{-8}$ or $10^{-7}$ to $10^{-9}$ or $10^{-10}$ to $10^{-12}$ or $10^{-13}$ to $10^{-15}$ or $10^{-9}$ to $10^{-12}$ or $10^{-9}$ to $10^{-15}$. In various aspects, the $K_D$ of the antigen-binding proteins provided herein is within a range of about $1.0\times10^{-12}$ M to about $1.0\times10^{-8}$ M. In various aspects, the $K_D$ of the antigen-binding proteins is within a range of about $1.0\times10^{-11}$ M to about $1.0\times10^{-9}$ M.

In various aspects, the affinity of the antigen-binding proteins are measured or ranked using a flow cytometry- or Fluorescence-Activated Cell Sorting (FACS)-based assay. Flow cytometry-based binding assays are known in the art. See, e.g., Cedeno-Arias et al., Sci Pharm 79(3): 569-581 (2011); Rathanaswami et al., Analytical Biochem 373: 52-60 (2008); and Geuijen et al., J Immunol Methods 302(1-2): 68-77 (2005). In various aspects, the affinity of the antigen-binding proteins are measured or ranked using a competition assay as described in Trikha et al., Int J Cancer 110: 326-335 (2004) and Tam et al., Circulation 98(11): 1085-1091 (1998). In Trikh et al., cells that express the antigen were used in a radioassay. The binding of $^{125}$I-labeled antigen-binding protein (e.g., antibody) to the cell surface antigen is measured with the cells in suspension. In various aspects, the relative affinity of a Mcl-1 antibody is determined via a FACS-based assay in which different concentrations of a Mcl-1 antibody conjugated to a fluorophore are incubated with cells expressing Mcl-1 and the fluorescence emitted (which is a direct measure of antibody-antigen binding) is determined. A curve plotting the fluorescence for each dose or concentration is made. The max value is the lowest concentration at which the fluorescence plateaus or reaches a maximum, which is when binding saturation occurs. Half of the max value is considered an $EC_{50}$ or an $IC_{50}$ and the antibody with the lowest $EC_{50}/IC_{50}$ is considered to have the highest affinity relative to other antibodies tested in the same manner.

In various aspects, the $IC_{50}$ value, as determined in a competitive binding inhibition assay, approximates the $K_D$ of the antigen-binding protein. In various instances, the competition assay is a FACS-based assay carried out with a reference antibody, fluorophore-conjugated secondary antibody, and cells which express Mcl-1. In various aspects, the cells are genetically engineered to overexpress Mcl-1. In some aspects, the cells are HEK293T cells transduced with a viral vector to express Mcl-1. In alternative aspects, the cells endogenously express Mcl-1. Before the FACS-based assay is carried out, in some aspects, the cells which endogenously express Mcl-1 are pre-determined as low Mcl-1-expressing cells or high Mcl-1-expressing cells. In some aspects, the cells are cancer or tumor cells. In various aspects, the cells are cells from a cell line, e.g., a blood cell line, an ovarian cell line, endometrial cell line, bladder cell line, lung cell line, gastrointestinal (GI) cell line, liver cell line, lung cell line, and the like. In various assays of the antigen-binding proteins of the disclosure, the antigen-binding proteins compete with a reference antibody for binding to human Mcl-1. A reduction in the binding of the reference antibody indicates the presence, strength, and/or degree of binding of an antigen-binding protein of the disclosure to Mcl-1, as determined by an in vitro competitive binding assay. In various aspects, the antigen-binding proteins of the disclosure inhibit the binding interaction between human Mcl-1 and the reference antibody and the inhibition is characterized by an $IC_{50}$. In various aspects, the antigen-binding proteins exhibit an $IC_{50}$ of less than about 2500 nM for inhibiting the binding interaction between human Mcl-1 and the reference antibody. In various aspects, the antigen-binding proteins exhibit an $IC_{50}$ of less than about 2000 nM, less than about 1500 nM, less than about 1000 nM, less than about 900 nm, less than about 800 nm, less than about 700 nm, less than about 600 nm, less than about 500 nm, less than about 400 nm, less than about 300 nm, less than about 200 nm, or less than about 100 nm. In various aspects, the antigen-binding proteins exhibit an $IC_{50}$ of less than about 90 nM, less than about 80 nM, less than about 70 nM, less than about 60 nM, less than about 50 nM, less than about 40 nM, less than about 30 nM, less than about 20 nM, or less than about 10 nM. In various instances, the antigen binding proteins of the disclosure compete against a reference antibody known to bind to Mcl-1 (which reference antibody is different from any of the antigen-binding proteins of the disclosure) for binding to Mcl-1.

Avidity gives a measure of the overall strength of an antibody-antigen complex. It is dependent on three major parameters: affinity of the antigen-binding protein for the epitope, valency of both the antigen-binding protein and Mcl-1, and structural arrangement of the parts that interact. The greater the valency (number of antigen binding sites) of an antigen-binding protein, the greater the amount of antigen (Mcl-1) it can bind. In various aspects, the antigen-binding proteins have a strong avidity for Mcl-1. In various aspects, the antigen-binding proteins are multivalent. In various aspects, the antigen-binding proteins are bivalent. In various instances, the antigen antigen-binding proteins are monovalent.

Cross-Reactivity

In various embodiments, the antigen-binding proteins of the disclosure bind to Mcl-1 and do not bind to any other member of the Bcl-2 family, i.e., do not cross-react with any other member of the Bcl-2 family. In various instances, the antigen-binding proteins of the disclosure are Mcl-1-specific. In various embodiments, the antigen-binding proteins of the present disclosure have a selectivity for Mcl-1 which is at least 10-fold, 5-fold, 4-fold, 3-fold, 2-fold greater than the selectivity of the antigen-binding protein for another protein of the Bcl-2 family. In various embodiments, the antigen-binding proteins of the disclosure have a selectivity for Mcl-1 which is at least 10-fold, 5-fold, 4-fold, 3-fold, 2-fold greater than the selectivity of the antigen-binding protein for any other Bcl-2 family protein. Selectivity may be based on the $K_D$ exhibited by the antigen binding protein for Mcl-1, or a Bcl-2 family member, wherein the $K_D$ may be determined by techniques known in the art, such as surface plasmon resonance or FACS-based affinity assays.

Competition Assays

In various embodiments, the antigen-binding protein inhibits a binding interaction between human Mcl-1 and a reference antibody, which reference antibody is known to bind to Mcl-1 but is not an antigen-binding protein of the disclosure. In various instances, the antigen-binding proteins of the disclosure compete with the reference antibody for binding to human Mcl-1, thereby reducing the amount of human Mcl-1 bound to the reference antibody as determined by an in vitro competitive binding assay. In various aspects, the antigen-binding proteins of the disclosure inhibit the binding interaction between human Mcl-1 and the reference antibody and the inhibition is characterized by an $IC_{50}$. In various aspects, the antigen-binding proteins exhibit an $IC_{50}$ of less than about 2500 nM for inhibiting the binding interaction between human Mcl-1 and the reference antibody. In various aspects, the antigen-binding proteins exhibit an $IC_{50}$ of less than about 2000 nM, less than about 1500 nM, less than about 1000 nM, less than about 900 nm, less than about 800 nm, less than about 700 nm, less than about 600 nm, less than about 500 nm, less than about 400 nm, less than about 300 nm, less than about 200 nm, or less than about 100 nm. In various aspects, the antigen-binding proteins exhibit an $IC_{50}$ of less than about 90 nM, less than about 80 nM, less than about 70 nM, less than about 60 nM, less than about 50 nM, less than about 40 nM, less than about 30 nM, less than about 20 nM, or less than about 10 nM.

In various instances, the antigen-binding proteins of the disclosure compete with the reference antibody for binding to human Mcl-1 and thereby reduce the amount of human Mcl-1 bound to the reference antibody, as determined by an in vitro competitive binding assay. In various aspects, the in vitro competitive binding assay is a FACS-based assay in which the fluorescence of a fluorophore-conjugated secondary antibody that binds to the Fc of the reference antibody is measured in the absence or presence of a particular amount of the antigen-binding protein of the disclosure. In various aspects, the FACS-based assay is carried out with the reference antibody, fluorophore-conjugated secondary antibody and cells that express Mcl-1. In various aspects, the cells are genetically engineered to overexpress Mcl-1. In some aspects, the cells are HEK293T cells transduced with a viral vector to express Mcl-1. In alternative aspects, the cells endogenously express Mcl-1. Before the FACS-based assay is carried out, in some aspects, the cells which endogenously express Mcl-1 are pre-determined as low Mcl-1-expressing cells or high Mcl-1-expressing cells. In some aspects, the cells are cancer or tumor cells. In various aspects, the cells are cells from a cell line, e.g., a blood cell line, an ovarian cell line, endometrial cell line, bladder cell line, lung cell line, gastrointestinal (GI) cell line, liver cell line, lung cell line, and the like. In various instances, the antigen binding proteins of the present disclosure bind with high affinity to Mcl-1 endogenously expressed by one or more of the cells that endogenously express Mcl-1. In various aspects, the antigen binding proteins exhibit an $IC_{50}$ of less than about 3000 nM as determined in a FACS-based competitive binding inhibition assay. In various aspects, the antigen binding proteins exhibit an $IC_{50}$ of less than about 2500 nM, less than about 2000 nM, less than about 1750 nM, less than about 1500 nM, less than about 1250 nM, less than about 1000 nM, less than about 750 nM, or less than about 500 nM, as determined in a FACS-based competitive binding inhibition assay. In various aspects, the antigen binding proteins exhibit an $IC_{50}$ of less than about 400 nM, less than about 300 nM, less than about 200 nM, less than about 100 nM, less than about 75 nM, less than about 50 nM, less than about 25 nM, or less than about 10 nM, as determined in a FACS-based competitive binding inhibition assay.

Other binding assays, such as competitive binding assays or competition assays that test the ability of an antibody to compete with a second antibody for binding to an antigen, or to an epitope thereof, are known in the art. See, e.g., Trikha et al., Int J Cancer 110: 326-335 (2004); Tam et al., Circulation 98(11): 1085-1091 (1998). U.S. Patent Application Publication No. US20140178905, Chand et al., Biologicals 46: 168-171 (2017); Liu et al., Anal Biochem 525: 89-91 (2017); and Goolia et al., J Vet Diagn Invest 29(2): 250-253 (2017). Also, other methods of comparing two antibodies are known in the art including, for example, surface plasmon resonance (SPR). SPR can be used to determine the binding constants of the antigen-binding protein of the disclosure and a reference antibody and the two binding constants can be compared.

Methods of Antibody Production and Related Methods

Suitable methods of making antigen-binding proteins (e.g., antibodies, antigen-binding antibody fragments, and antibody protein products) are known in the art. For instance, standard hybridoma methods for producing antibodies are described in, e.g., Harlow and Lane (eds.), Antibodies: A Laboratory Manual, CSH Press (1988), and C A. Janeway et al. (eds.), Immunobiology, $5^{th}$ Ed., Garland Publishing, New York, NY (2001)).

Depending on the host species, various adjuvants can be used to increase the immunological response leading to greater antibody production by the host. Such adjuvants include, but are not limited to, Freund's complete and incomplete adjuvants, mineral gels such as aluminum hydroxide, and surface-active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Other methods of antibody production are summarized in Table 1.

TABLE 1

| Technique | Various references |
|---|---|
| EBV-hybridoma methods and Bacteriophage vector expression systems | Haskard and Archer, J. Immunol. Methods, 74(2), 361-67 (1984), Roder et al., Methods Enzymol., 121, 140-67 (1986), and Huse et al., Science, 246, 1275-81 (1989)). |
| methods of producing antibodies in non-human animals | U.S. Pat. Nos. 5,545,806, 5,569,825, and 5,714,352, and U.S. Patent Application Publication No. 2002/0197266 |
| inducing in vivo production in the lymphocyte population or by screening recombinant immunoglobulin libraries or panels of highly specific binding reagents | Orlandi et al (Proc Natl Acad Sci 86: 3833-3837; 1989), and Winter G and Milstein C (Nature 349: 293-299, 1991). |
| methods of producing recombinant proteins | Protein production and purification" Nat Methods 5(2): 135-146 (2008). |
| Phage display | Janeway et al., supra, Huse et al., supra, and U.S. Pat. No. 6,265,150). Related methods also are described in U.S. Pat. No. 5,403,484; U.S. Pat. No. 5,571,698; U.S. Pat. No. 5,837,500; U.S. Pat. No. 5,702,892. The techniques described in U.S. Pat. No. 5,780,279; U.S. Pat. No. 5,821,047; U.S. Pat. No. 5,824,520; U.S. Pat. No. 5,855,885; U.S. Pat. No. 5,858,657; U.S. Pat. No. 5,871,907; U.S. Pat. No. 5,969,108; U.S. Pat. No. 6,057,098; and U.S. Pat. No. 6,225,447 |
| Antibodies can be produced by transgenic mice | U.S. Pat. Nos. 5,545,806 and 5,569,825, and Janeway et al., supra. |

Methods of testing antibodies for the ability to bind to the epitope of Mcl-1, regardless of how the antibodies are produced, are known in the art and include any antibody-antigen binding assay such as, for example, radioimmunoassay (RIA), ELISA, Western blot, immunoprecipitation, SPR, and competitive inhibition assays (see, e.g., Janeway et al., and U.S. Patent Application Publication No. 2002/0197266).

In certain embodiments, antibody variants include glycosylation variants wherein the number and/or type of glycosylation site(s) has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-Xaa-Ser or Asn-Xaa-Thr, wherein the amino acid residue designated as Xaa may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional antibody variants include cysteine variants, wherein one or more cysteine residues are deleted from, or substituted for, another amino acid (e.g., serine) compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

In additional embodiments, antibody variants can include antibodies comprising a modified Fc fragment or a modified heavy chain constant region. An Fc fragment, which stands for "fragment that crystallizes," or a heavy chain constant region can be modified by mutation to confer on an antibody altered binding characteristics. See, for example, Burton and Woof 1992, Advances in Immunology 51: 1-84; Ravetch and Bolland, 2001, Annu. Rev. 19: 275-90, Shields et al., 2001, Journal of Biol. Chem 276: 6591-6604; Telleman and Junghans, 2000, Immunology 100: 245-251; Medesan et al., 1998, Eur. J. Immunol. 28: 2092-2100; all of which are incorporated herein by reference). Such mutations can include substitutions, additions, deletions, or any combination thereof and are typically produced by site-directed mutagenesis using one or more mutagenic oligonucleotide(s) according to methods described herein, as well as according to methods known in the art (see, for example, Sambrook et al., MOLECULAR CLONING: A LABORATORY MANUAL, 3rd Ed., 2001, Cold Spring Harbor, N.Y. and Berger et al., METHODS IN ENZYMOLOGY, Volume 152, Guide to Molecular Cloning Techniques, 1987, Academic Press, Inc., San Diego, Calif., which are incorporated herein by reference).

According to certain embodiments, amino acid substitutions may (1) reduce susceptibility to proteolysis, (2) reduce susceptibility to oxidation, (3) alter binding affinity, and/or (4) confer or modify other physicochemical or functional properties on such polypeptides. According to certain embodiments, single or multiple amino acid substitutions (in certain embodiments, conservative amino acid substitutions) may be made in the naturally occurring sequence (in certain embodiments, in the portion of the polypeptide outside the domain(s) forming intermolecular contacts). In certain embodiments, a conservative amino acid substitution typically does not substantially change the structural characteristics of the parent sequence (e.g., a conservative replacement amino acid does not disrupt or tend to disrupt secondary structure that characterizes a parent sequence, such as a helix). Examples of art-recognized polypeptide secondary and tertiary structures are described in PROTEINS, STRUCTURES AND MOLECULAR PRIN- CIPLES, (Creighton, Ed.), 1984, W. H. Freeman and Company, New York; in INTRODUCTION TO PROTEIN STRUCTURE (C. Branden and J. Tooze, eds.), 1991, Garland Publishing, New York, N.Y.; and in Thornton et al., 1991, Nature 354:105, each of which is incorporated herein by reference.

The disclosure provides antibodies that comprise a heavy chain and a light chain, wherein the heavy and light chains together form an antigen binding structure capable of specifically binding Mcl-1. A full-length heavy chain includes a variable region domain, $V_H$, and three constant region domains, $C_{H1}$, $C_{H2}$, and $C_{H3}$. Typically, the $V_H$ domain is at the amino-terminus of the polypeptide and the $C_H$ domain is at the carboxyl-terminus. The term "heavy chain", as used herein, encompasses a full-length heavy chain and fragments thereof. A full-length light chain includes a variable region domain, $V_L$, and a constant region domain, $C_L$. Like the heavy chain, the variable region domain of the light chain is typically at the amino-terminus of the polypeptide. The term "light chain", as used herein, encompasses a full-length light chain and fragments thereof. A F(ab) fragment is comprised of one light chain and the $C_{H1}$ and variable regions of one heavy chain. The heavy chain of a F(ab) molecule cannot form a disulfide bond with another heavy chain molecule. A F(ab') fragment contains one light chain and one heavy chain that contains more of the constant region, between the $C_{H1}$ and $C_{H2}$ domains, such that an interchain disulfide bond can be formed between two heavy chains to form a $F(ab')_2$ molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain, which forms an antigen-binding region. Single-chain antibodies are discussed in detail in WO 88/01649 and U.S. Pat. Nos. 4,946,778 and 5,260,203, incorporated herein in relevant part by reference.

The following examples are presented by way of illustration and are not intended to limit the scope of the subject matter disclosed herein.

EXAMPLES

Example 1

Rabbit Immunizations—Rabbit Clonal Expansion Direct Rescue (CEDR): Harvest, Sorts, Supernatant, and Lysate Generation Rabbits were immunized with Mcl-1 using a protocol that is standard in the art. Animal spleens were harvested, dissociated and frozen. Thawed rabbit immune cells were probed with biotinylated Mcl-1 and streptavidin conjugated to Alexa Fluor 647 as well as anti-rabbit IgG antibody conjugated to Alexa Fluor 488 to identify cells expressing Mcl-1 antibodies. Detected cells were then sorted on FACS Aria III into 384 well plates containing 100 μl/well RPMI media supplemented with FBS, 10% activated rabbit splenocyte supernatant (TSN), and feeder cell culture. After 7 days in monoclonal culture and B-cell expansion, culture supernatants were collected for subsequent assays and rabbit B-cells were lysed for sequencing and recombinant rescue of antibody sequences.

Figure 4:
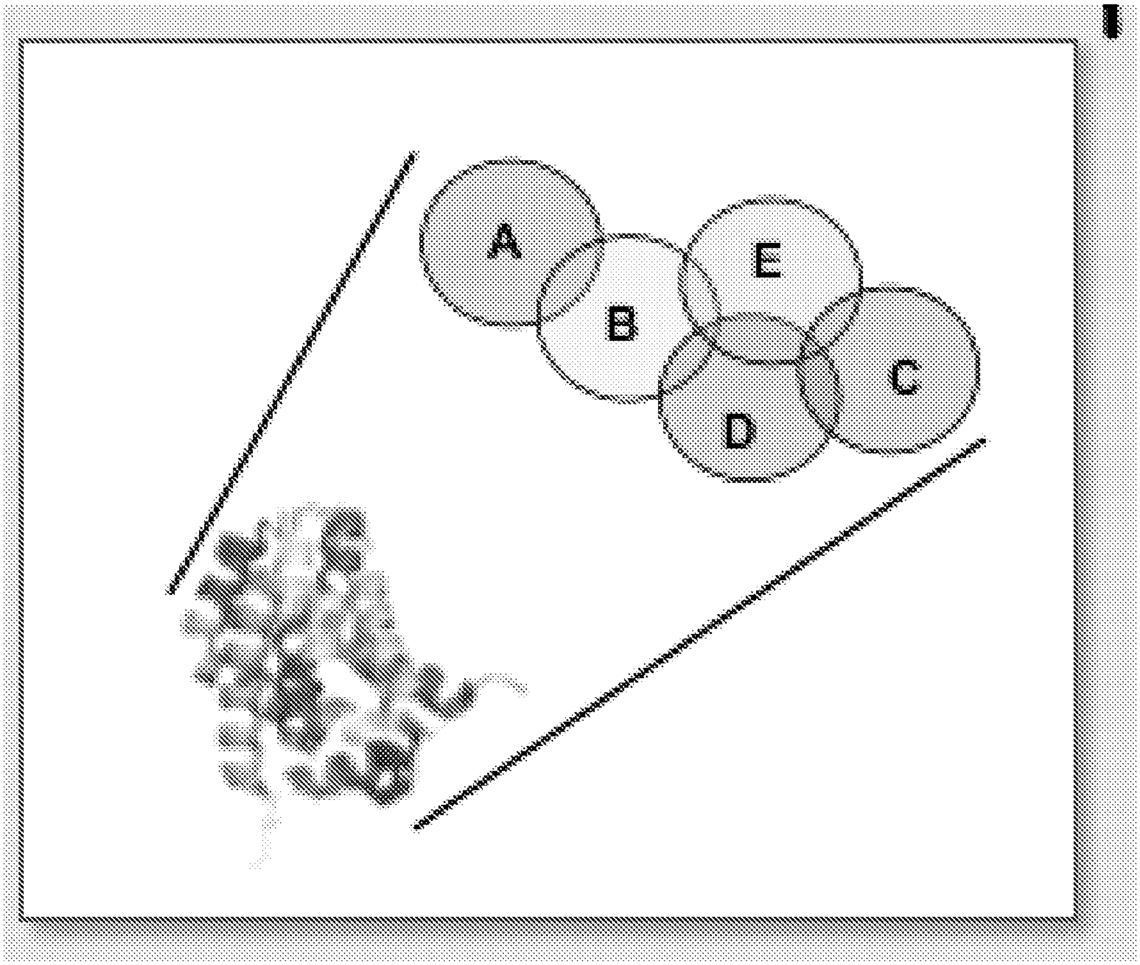
FIG. 4. High-throughput epitope binning identified 5 bins. The panel of anti-Mcl-1 antibodies identified in FIG. 3 were binned against each other to create a conceptual epitope space map.
Figure 5:
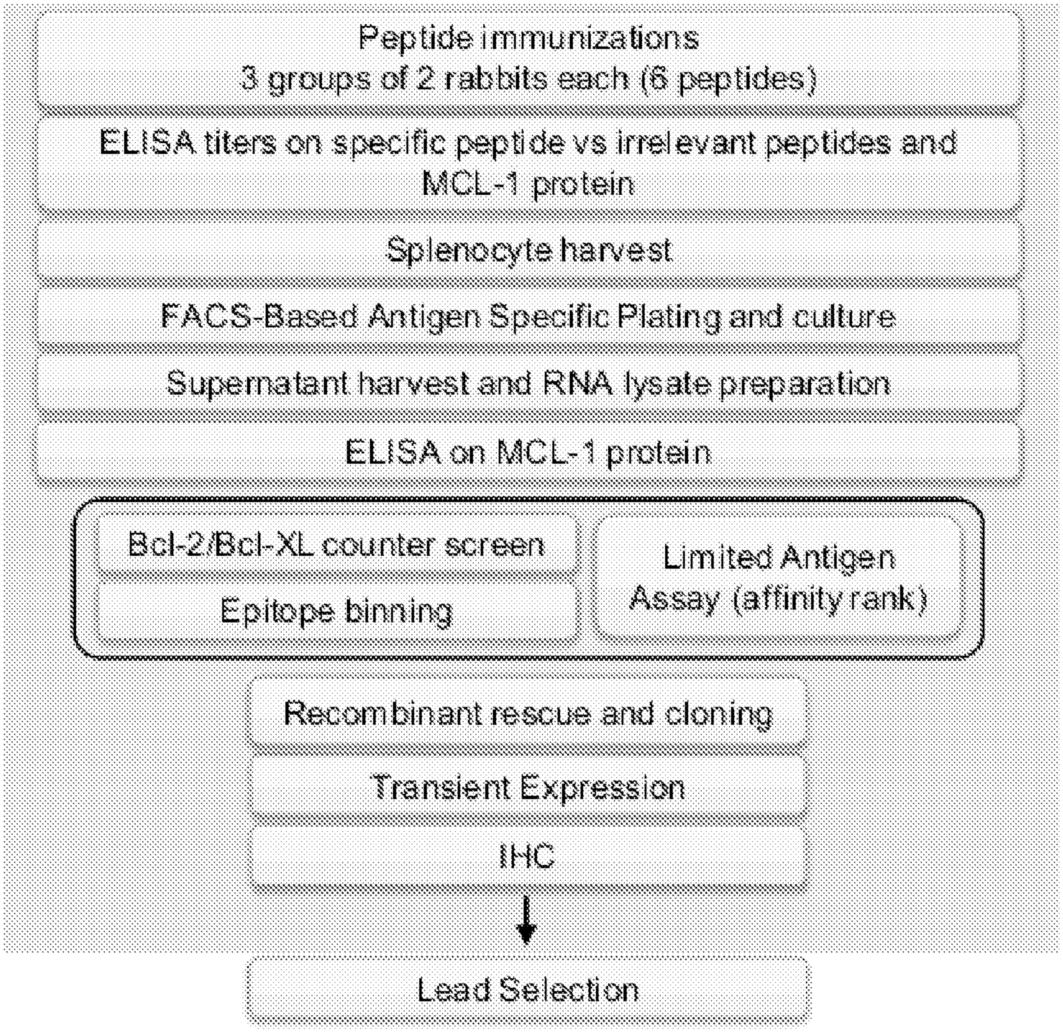
FIG. 5. Rabbit Clonal Expansion Direct Rescue (CEDR) workflow in support of biomarker development of AMG176, an Mcl-1 inhibitor. Rabbits were immunized using a standard protocol known in the art. In brief, animal spleens were harvested, dissociated, and the single-cell suspensions were frozen. Thawed rabbit splenocytes were single cell-sorted on FACS Aria III into 384-well plates on biotinylated Mcl-1 protein and detected by streptavidin conjugated to Alexa Fluor 647 and on anti-rabbit IgG antibody conjugated to Alexa Fluor 488. The cells were sorted into 100 µl/well RPMI media supplemented with FBS, 10% activated rabbit splenocyte supernatant (TSN), and feeder cell culture. After 7 days in monoclonal culture and B-cell expansion, culture supernatants were collected for subsequent assays and rabbit B-cells were lysed for sequencing and recombinant rescue of antibody sequences. Highest-affinity, Mcl-1-selective, representative antibodies from each epitope bin were selected for cloning and expression. These antibodies were assayed immunohistochemically (IHC), and antibody lead compounds 11P5 and 11B14 were identified. 11P5 was selected to move forward for Companion Diagnostics (CDx) assay development.
Figure 6:
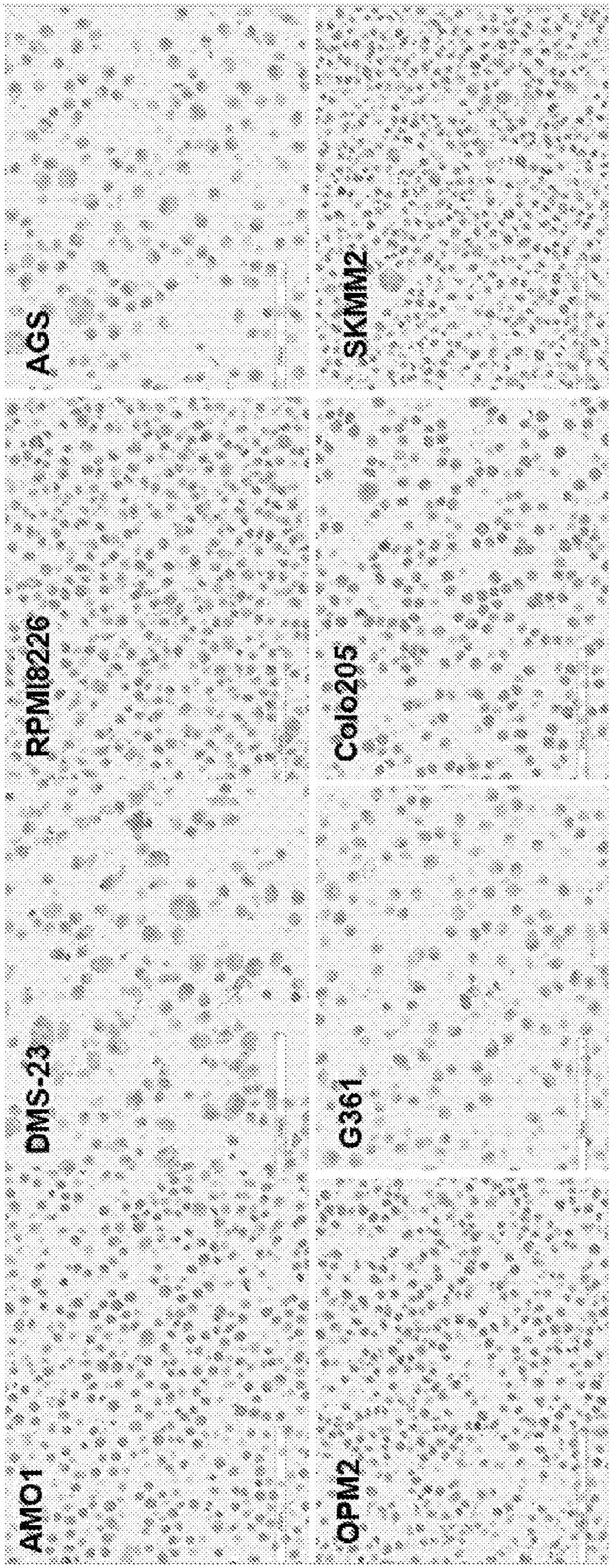
FIG. 6. A rabbit isotype control contained IgG antibodies from rabbits that were not immunized with Mcl-1. These rabbit isotype control antibodies were useful in assessing the anti-Mcl-1 antibodies generated by the methods disclosed herein. Rabbit isotype control antibodies at 5 μg/ml were used to probe the eight cell types as shown in panels A-H. A) AMO1, B) DMS-23, C) RPM18226, D) AGS, E) QPM2, F) G361, G) Colo205, and H) SKMM2.
Figure 7:
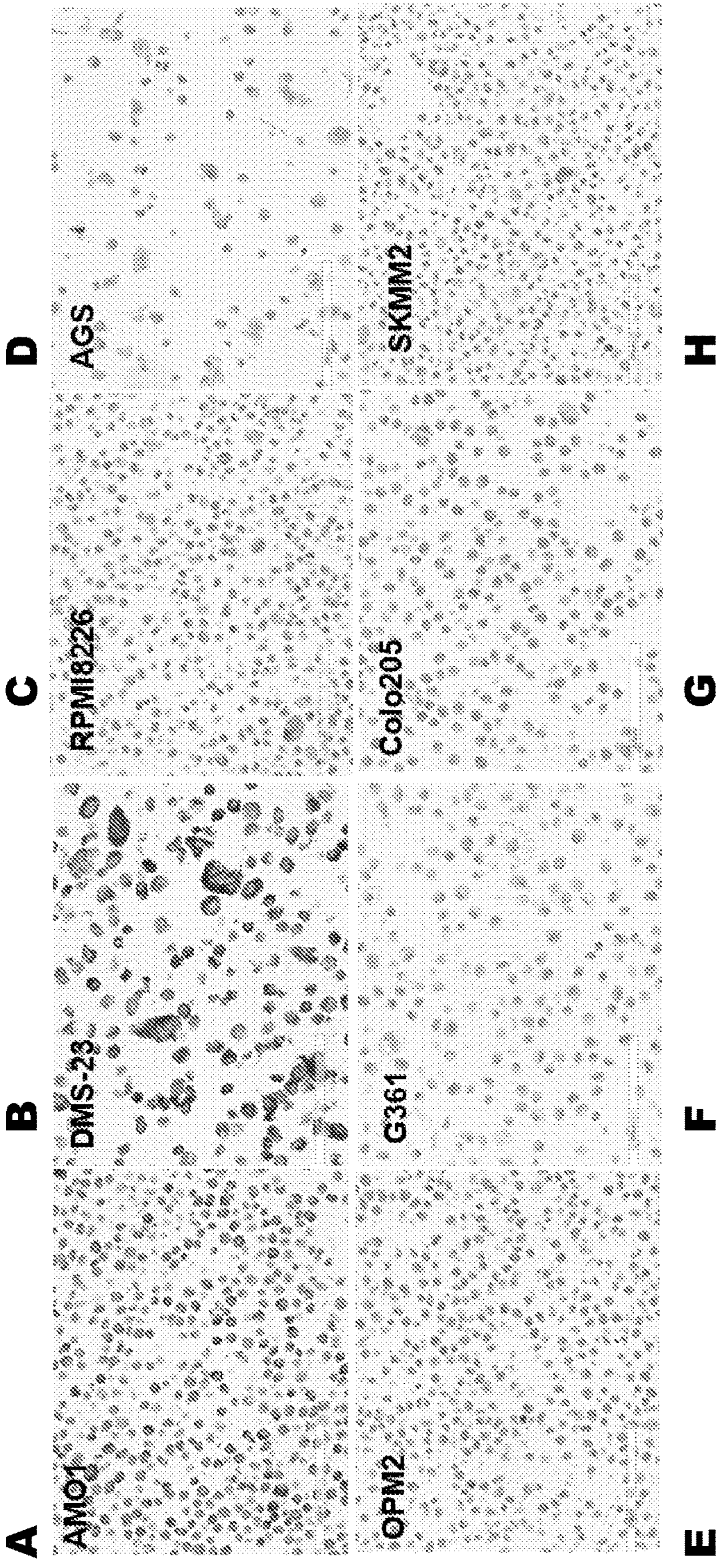
FIG. 7. Anti-Mcl-1 antibody 4019 at 1 μg/ml was used to probe the eight cell types as shown in panels A-H. A) AMO1, B) DMS-23, C) RPM18226, D) AGS, E) QPM2, F) G361, G) Colo205, and H) SKMM2.
Figure 8:
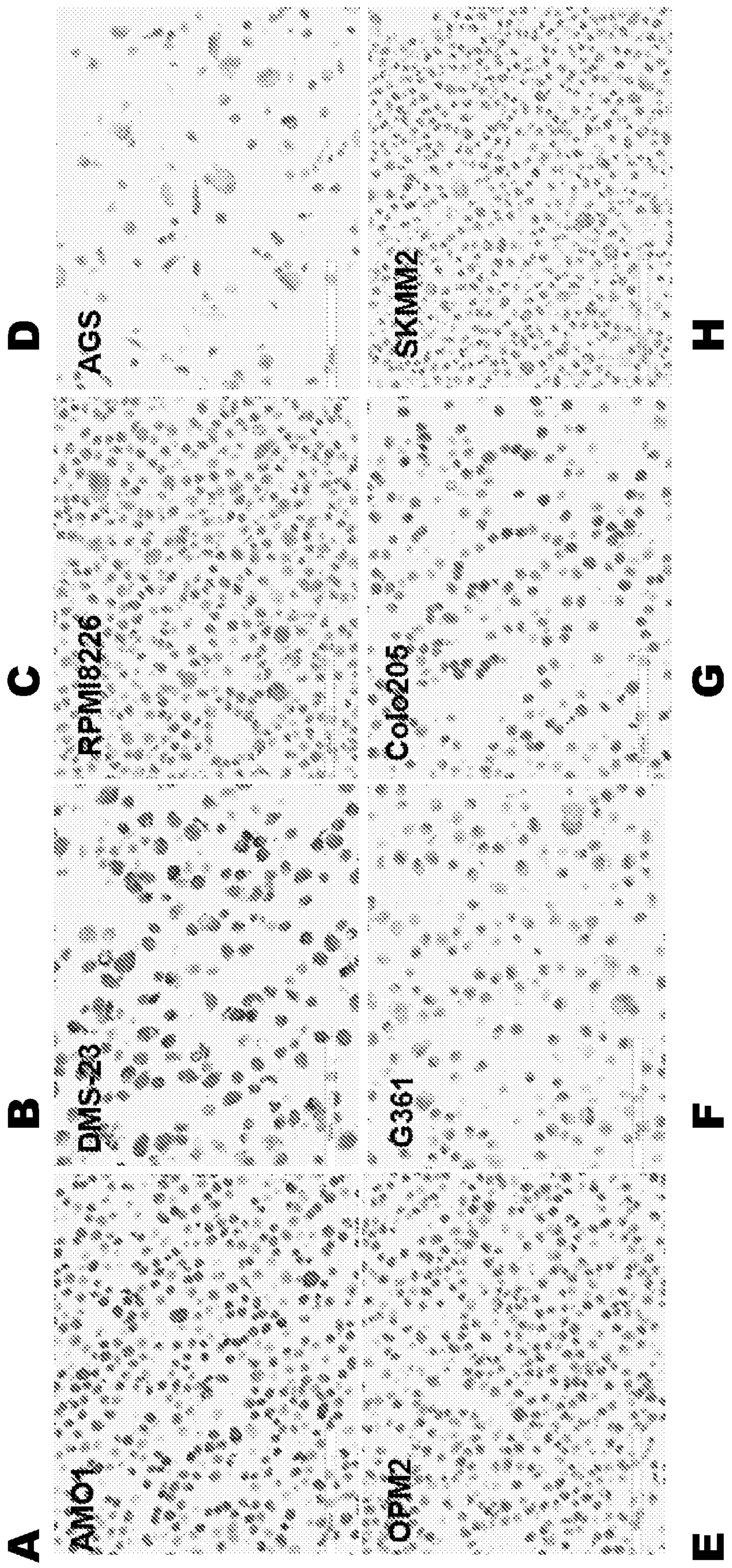
FIG. 8. Anti-Mcl-1 antibody 5H16 at 5 μg/ml was used to probe the eight cell types as shown in panels A-H. A) AMO1, B) DMS-23, C) RPM18226, D) AGS, E) QPM2, F) G361, G) Colo205, and H) SKMM2.
Figure 9:
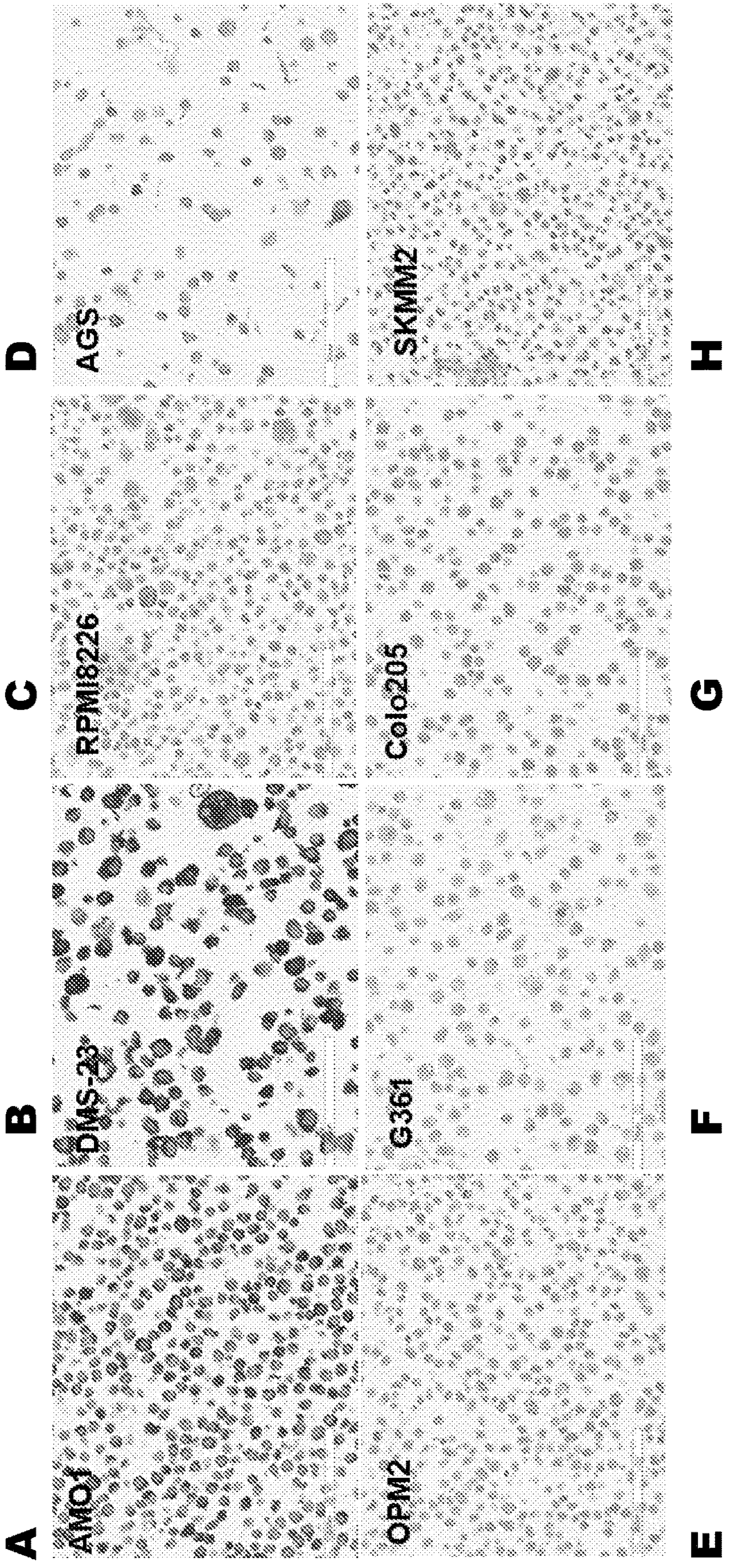
FIG. 9. Anti-Mcl-1 antibody 6A3 at 1 μg/ml was used to probe the eight cell types as shown in panels A-H. A) AMO1, B) DMS-23, C) RPM18226, D) AGS, E) QPM2, F) G361, G) Colo205, and H) SKMM2.

Highest affinity, Mcl-1-selective representative antibodies from each epitope bin (see FIG. 4) were selected for cloning and expression. These antibodies were assayed immunohistochemically (IHC), which identified anti-Mcl-1 antibody leads 11P5 and 11B14.

To recombinantly rescue antibodies from lysed B-cells, lysate was initially purified using the mRNA Catcher PLUS purification kit (lnvitrogen/Thermo Fisher). Following this purification step, cDNA was synthesized and antibody sequences were amplified using rabbit IgG-specific primers. Antibody sequences were analyzed, and unique sequences were chosen for cloning. Sequences were cloned into an expression vector pTT5 and expressed in HEK293T cells using the 293fectin transient transfection system following the procedure provided by the manufacturer (Thermo Fisher). IHC assays were used to confirm that the purified antibodies selectively bound Mcl-1 protein. The 11P5 anti-Mcl-1 antibody was selected for companion diagnostic (CDx) development.

TABLE 2

(primers)

| | Sequence 5' to 3' | Sequence identifier |
|---|---|---|
| Rabbit VK PCR amplification primers | | |
| Rab Ck, Rabbit Vk AS-RT primer | 5' CCA GGT GAC GGT 3' | 34 |
| Rab Vk 5'UTR, Rabbit VK S-outer primer | 5' AG[GA]ACC CAG CAT GGA CA[CT][CGA]A 3' | 35 |
| Rab Ck, Rabbit Vk AS-outer primer | 5' GGA[TC][AG]G[AT]AT TTA TT[CT]GCC AC[GA]CAC A 3' | 36 |
| Rabbit VH PCR amplification primers | | |
| Rab Cg CH1, Rabbit Vg AS-RT primer | 5' TGC CCG AGT TCC A 3' | 37 |
| Rab VH 5'UTR, Rabbit VH S-outer primer | 5' AGA C[GA]C TCA CCA TGG AGA CT 3' | 38 |
| Rab Cg, Rabbit Vg AS-outer primer | 5' ACT GGC TCC GGG AGG TA 3' | 39 |

Example 2

ELISA on Mcl-1 Protein

Cell culture supernatants from B-cells isolated from immune rabbits, comprising rabbit monoclonal antibodies, were screened for binding to Mcl-1 protein by enzyme-linked immunosorbent assay (ELISA). The wells of medium-binding plates were first coated with Neutravidin overnight at 4° C., washed 3× with 90 μL PBS using a BioTek plate washer and then blocked with a 1% milk/1× PBS assay diluent. Biotinylated Mcl-1 was then immobilized in the wells of the neutravidin-coated medium-binding plates and washed 3× with PBS. Rabbit CEDR supernatants were then added at a 1:5 dilution in 50 μL assay volume for one hour at room temperature (RT). Bound antibodies were then identified with Horse Radish Peroxidase (HRP)-conjugated goat-anti-rabbit secondary antibody (Jackson ImmunoResearch) and 3,3',5,5'-Tetramethylbenzidine (TMD) (Neogen) substrate following the protocol set out by the manufacturer. Plate wells were subjected to absorbance measurements at 450 nm in a plate reader. The threshold for binding to immobilized Mcl-1 in this assay was a three-fold increase in absorbance compared to the absorbance measured in a well to which irrelevant (i.e., control) rabbit supernatant had been added.

Example 3

Bcl-2/Bcl-xL Counter Screen

Antibodies binding Mcl-1 were evaluated for cross-reactivity to Bcl-2 and Bcl-xL by ELiSA, In brief, Bcl-2 and Bcl-xL proteins were separately coated in wells of medium-binding plates for one hour at 37° C., washed 3× with 90 μL PBS using a BioTek plate washer, and then blocked with a 1% milk/1×PBS assay diluent. Rabbit CEDR supernatants were then added to the wells for one hour at RT. Bound antibodies were then identified with Horse Radish Peroxidase (HRP)-conjugated goat-anti-rabbit secondary antibody (Jackson ImmunoResearch) and TMB substrate following the protocol set out by the manufacturer. Rate wells were subjected to absorbance measurements at 450 nm in a plate reader. The threshold for binding to immobilized Bcl-2 or Bcl-xL in this assay was a three-fold increase in absorbance compared to the absorbance measured in a well to which irrelevant (i.e., control) rabbit supernatant had been added.

Example 4

Epitope Binning (Relative Epitope Binning/Profiling)

A common way to characterize epitopes is through competition experiments. Antibodies that compete with each other can be thought of as binding the same or overlapping site on the target. This example describes a method of determining competition for binding to Mcl-1 and the results of the method when applied to a number of antibodies is described.

Binning experiments can be conducted in a number of ways, and the method employed may have an effect on the assay results. In the binning experiments disclosed herein, Mcl-1 was bound by one reference antibody and probed by another. If the reference antibody prevented the binding of the probe antibody, the antibodies were categorized in the same bin. The order in which the antibodies were employed is important. If antibody A were employed as the reference antibody and blocked the binding of antibody B, the converse would not always be true: antibody B used as the reference antibody would not necessarily block antibody A binding to the target. There are a number of factors in play here: the binding of an antibody can cause conformational changes in the target that prevent the binding of the second antibody, or epitopes that overlap but do not completely occlude each other may allow for the second antibody to still have enough high-affinity interactions with the target to allow binding, in general, if competition is observed in either order, the antibodies are said to bin together, and if both antibodies can block each other then it is likely that the epitopes overlap more completely.

For the experiment described in this Example, a modified antibody-antibody competition assay was used to determine the relative epitope binning profiles of the Mcl-1-specific antibodies in a high throughput manner. Shay, each individual antibody was tested for its ability to compete for binding with a panel of reference antibodies chosen from an earlier Mcl-1 CEDR campaign that were sequence diverse. The pattern of competition/binding of each test antibody with the reference antibody panel was then determined and compared to those produced from the other test antibodies. The degree of correlation between the individual test antibody competition/binding profiles was then compared. Antibodies that showed similar competition/binding profiles were binned (grouped) together (e.g., Binning Profile A, B, etc.).

Biotinylated Mcl-1 protein was coupled to streptavidin coated, uniquely barcoded, LumAvidin Beads (Luminex Corporation) for 30 minutes in the dark at RT and washed twice with PBS+2% FBS (FACS buffer) by pelleting the beads with centrifugation. The reference antibody supernatant samples were incubated with the antigen-coated beads for one hour in the dark at RT and washed three times. Beads were resuspended in FACS buffer containing StabilGuard® to block nonspecific binding sites (Surmodics). The antigen-coated beads to which reference antibodies had bound were pooled and then divided into individual sample wells containing the test antibody (CEDR supernatant) sample (or negative control). The beads and test antibodies were incubated for one hour in the dark at RT and washed twice. Samples were then incubated with Alexa Fluor® 488 IgG fragment-specific detection antibody for 15 minutes in the dark at RT, washed once and resuspended in FACS buffer. Samples were analyzed using an iQue™ Screener Platform (Intellicyt).

To determine the antibody competition/binding profiles of the individual test antibodies, the reference-only antibody binding signal was subtracted from the reference plus test antibody signal for each competition/binding reaction (i.e., across the entire reference antibody set). An individual antibody binding profile was defined as the collection of net binding values for each competition/binding reaction. The degree of similarity between individual profiles was then assessed by calculating the correlation coefficient between each of the test antibody profiles. Test antibodies showing higher degrees of similarity to each other were then grouped into common binning profiles. Separate binning profiles exhibited a low degree of correlation. Using this method, the Mcl-1-binding antibodies were sub-divided into 5 unique binning profiles.

Example 5

Limited Antigen Assay (Affinity Rank)

To assess antibody and antigen interaction strength (relative binding affinity), Mcl-1-specific CEDR supernatants were tested in a limiting antigen-binding assay. Titrated small amounts of biotinylated Mcl-1 protein were incubated with streptayidin-coated LumAvidin Beads® (Luminex Corporation) for 30 minutes in the dark at RT and then washed twice with FACS buffer pelleting the beads with centrifugation. Beads were resuspended in FACS buffer containing StabilGuard® (Surmodics). Antigen-bound beads were then incubated with CEDR supernatant sample for 18 hours in the dark at RT, washed twice with FACS buffer, incubated with Alexa Fluor® 488 IgG fragment-specific detection antibody for 15 minutes in the dark at RT, washed once and finally resuspended in FACS buffer. Samples were analyzed using an iQue™ Screener Platform (Inteilicyt). In this assay method, the degree of antibody binding signal to the target (Mcl-1) correlates with the measured fluorescence intensity and thus allows a relative comparison of affinities across the panel.

Each of the references cited herein is hereby incorporated by reference in its entirety or in relevant part, as would be apparent from the context of the citation.

It is to be understood that, while the claimed subject matter has been described in conjunction with the detailed description thereof, the foregoing description is intended to illustrate and not limit the scope of that claimed subject matter, which is defined by the scope of the appended claims. Other aspects, advantages, and modifications are within the scope of the following claims.

Example 6

ImmunoHistoChemical Assays

Commercially available ImmunoHistoChemical (IHC) reagents were used for assessing Bcl-2 and Bcl-xL expression by IHC. The anti-Mcl-1 monoclonal antibody 11P5 disclosed herein was shown to sensitively and specifically bind to Mcl-1, including in tumor cell lines, whole tissues, and decalcified bone samples. Measurement of the expression level of Bcl-2 was achieved using anti-Bcl-2 monoclonal antibody (catalog no. MO887) clone 124 mouse IgG1 (Agilent DAKO) at 10 μg/mL. A qualified negative control was obtained by probing testis tissue. The expression level of Bcl-xL was measured using anti-Bcl-xL monoclonal antibody (catalog no. 2764) clone 54H6 rabbit IgG (Cell Signaling Technology) at 1:400 dilution. A qualified negative control involved probing the myometrial tissue of the uterus. Measurement of Mcl-1 expression was obtained using an anti-Mcl-1 rabbit IgG antibody (Amgen) at 0.25 μg/mL. Qualified negative controls involved probing testis and uterus tissues, as well as the SKMM2 cell line.

Figure 10:
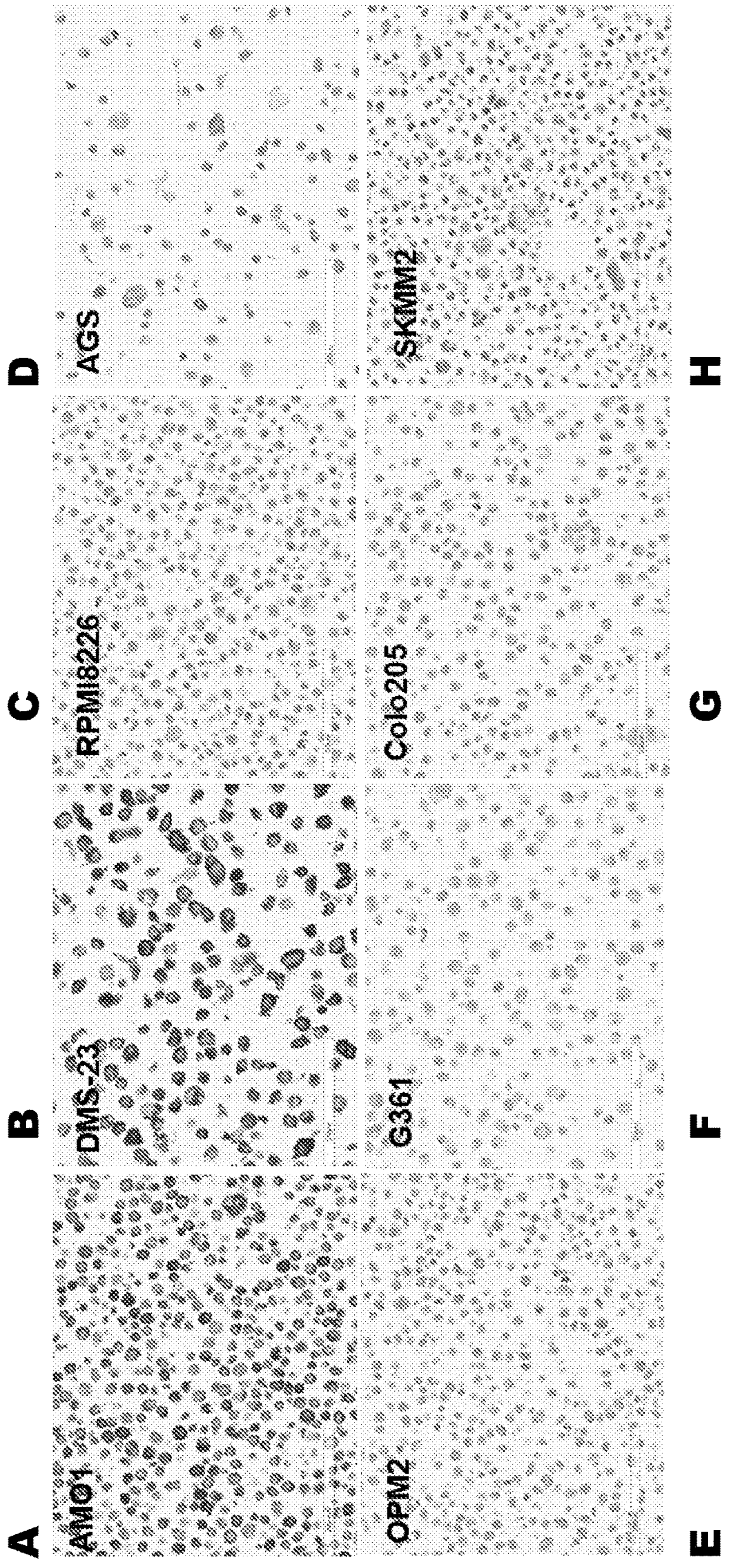
FIG. 10. Immunohistochemical analysis of tumor cell lines. Anti-Mcl-1 monoclonal antibody 11P5 was used at 1 μg/ml to probe eight different tumor cell lines, i.e., AMO1, DMS-23, RPM18226, AGS, QPM2, G361, Colo205, and SKMM2. Probed cells were formalin-fixed and paraffin-embedded (FFPE) using conventional techniques prior to being subjected to immunohistochemical staining and microscopic examination. The results reveal that antibody 11P5 exhibits specific cytoplasmic staining of each tested tumor cell line.
Figure 11:
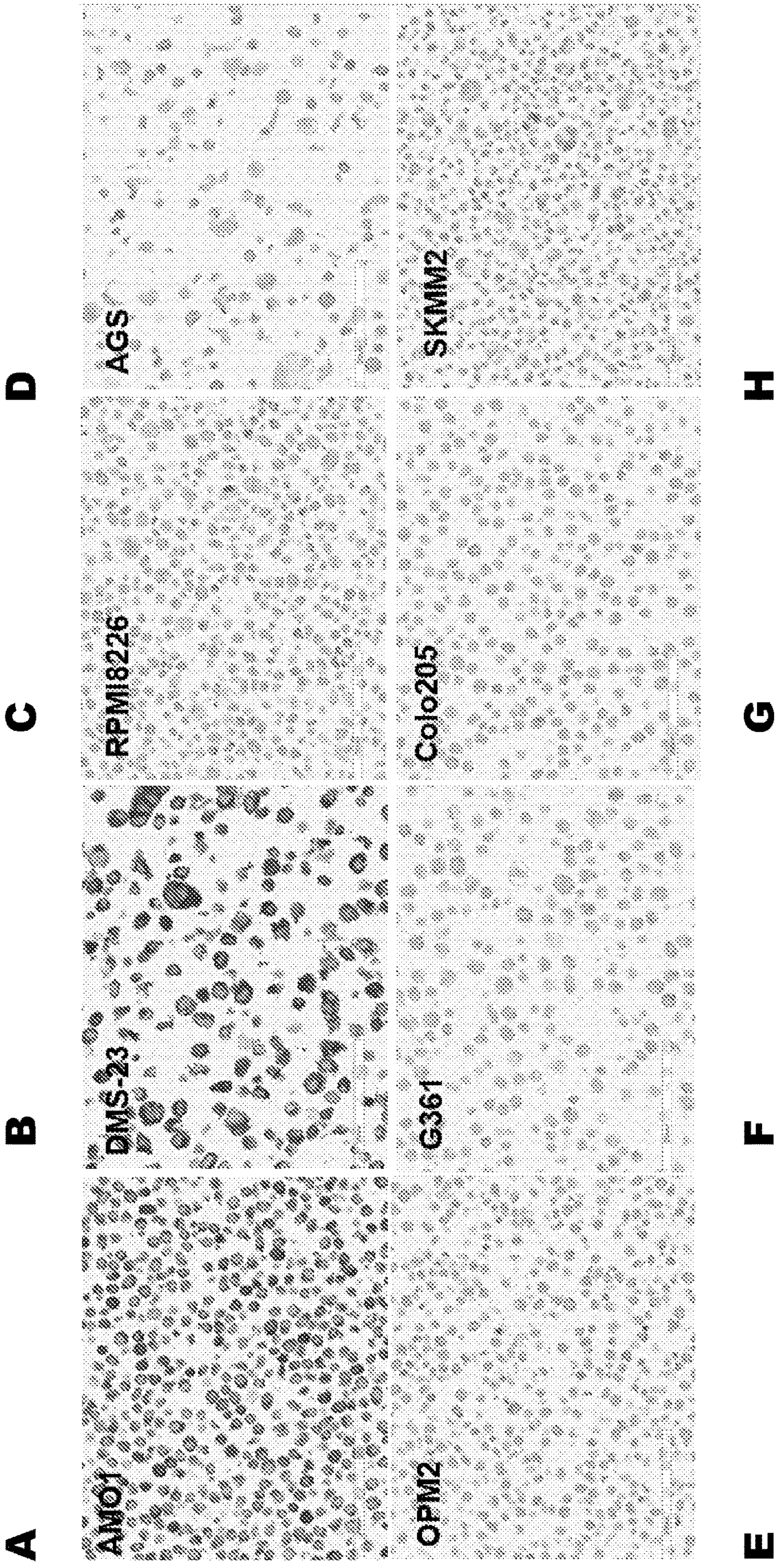
FIG. 11. Anti-Mcl-1 antibody 11B14 at 1 μg/ml was used to probe the eight cell types as shown in panels A-H. A) AMO1, B) DMS-23, C) RPM18226, D) AGS, E) QPM2, F) G361, G) Colo205, and H) SKMM2.
Figure 12:
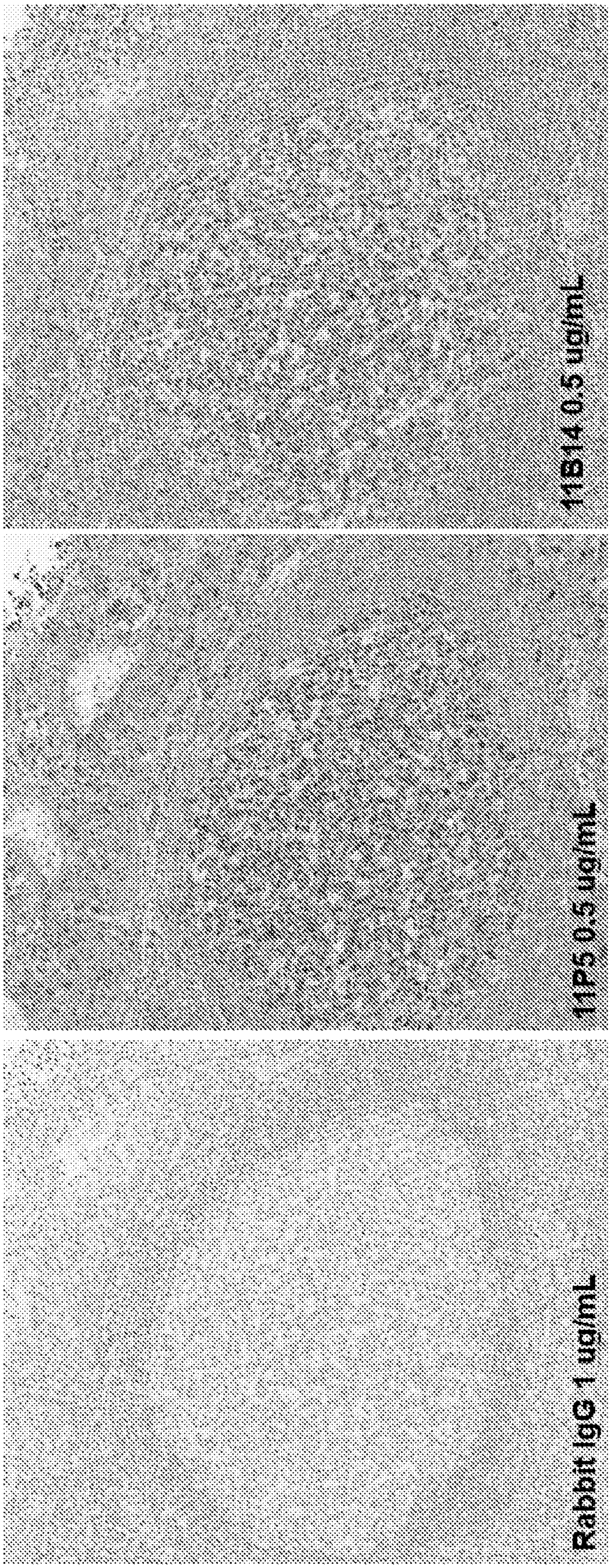
FIG. 12. Comparative antibody binding. A) Tonsil cells of patient 07H-3971 were subjected to immunohistochemical staining with rabbit isotype control antibodies at 1 μg/ml; B) Tonsil cells of patient 07H-3971 were subjected to immunohistochemical staining with anti-Mcl-1 antibody 11P5 at 0.5 μg/ml; C) Tonsil cells of patient 07H-3971 were subjected to immunohistochemical staining with anti-Mcl-1 antibody 11B14 at 0.5 μg/ml.
Figure 13:
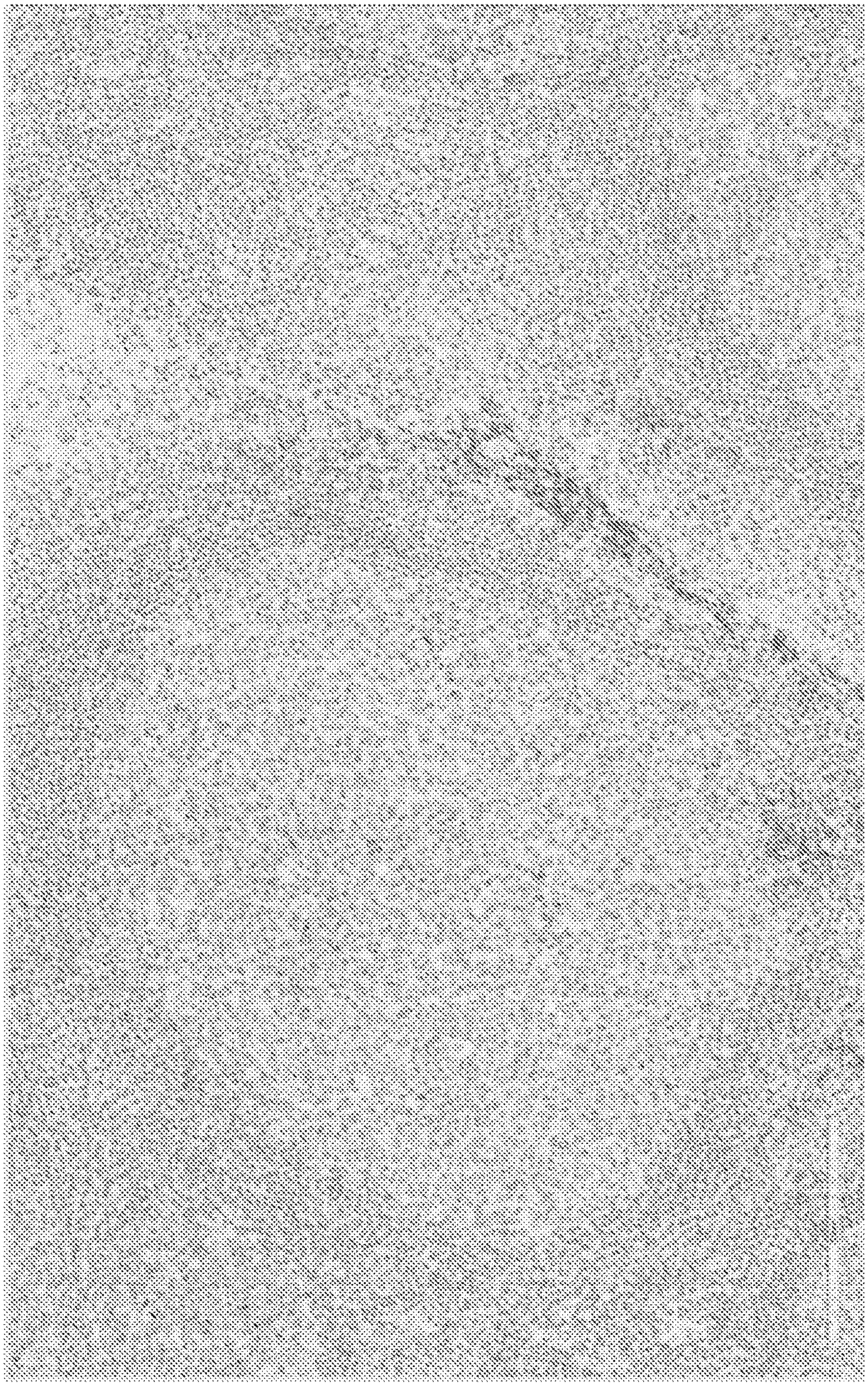
FIG. 13. Tonsil cells of patient 07H-3971 were subjected to immunohistochemical staining with anti-Mcl-1 antibody 4019 at 1.0 μg/ml.
Figure 14:
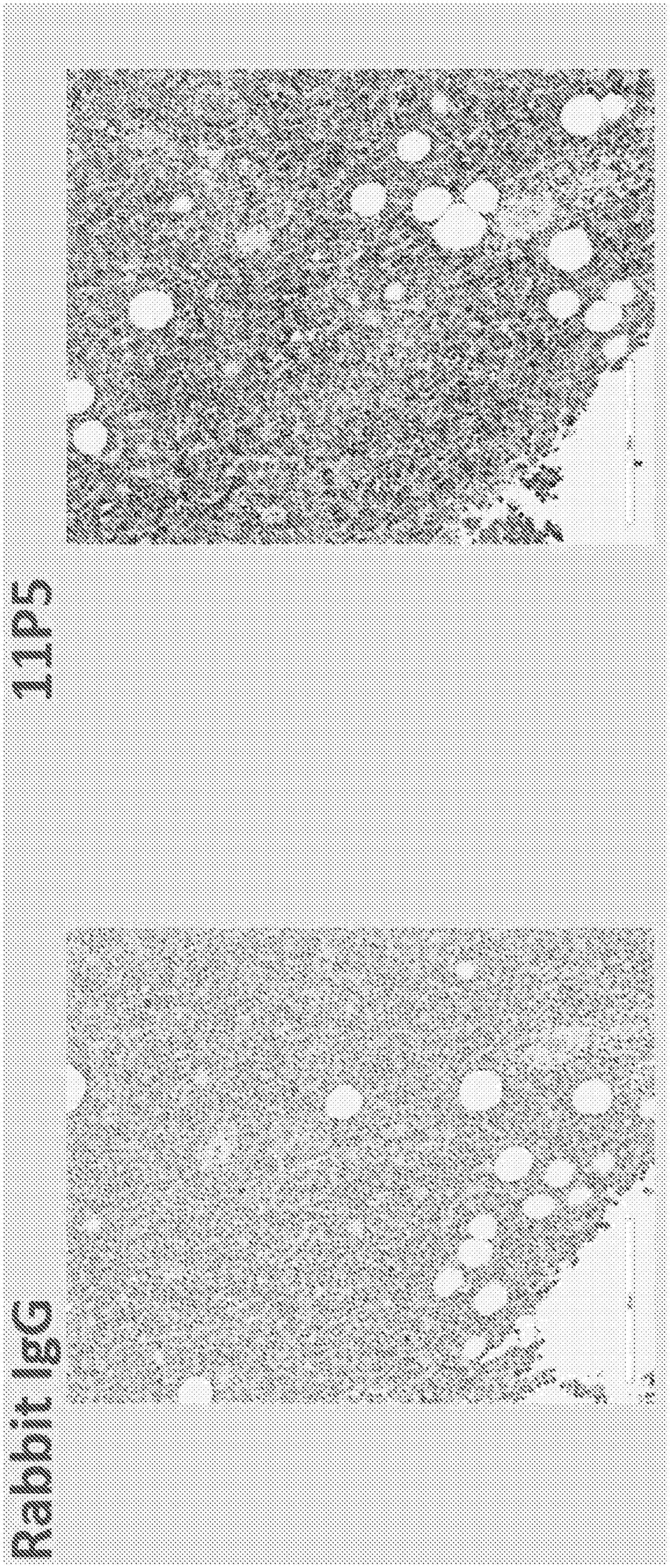
FIG. 14. Comparative antibody binding. Left panel: Bone marrow cells of patient 04H-391 were subjected to immunohistochemical staining with rabbit isotype control antibodies at 1 μg/ml; B) Bone marrow cells of patient 04H-391 were subjected to immunohistochemical staining with anti-Mcl-1 antibody 11P5 at 0.5 μg/ml.
Figure 15:
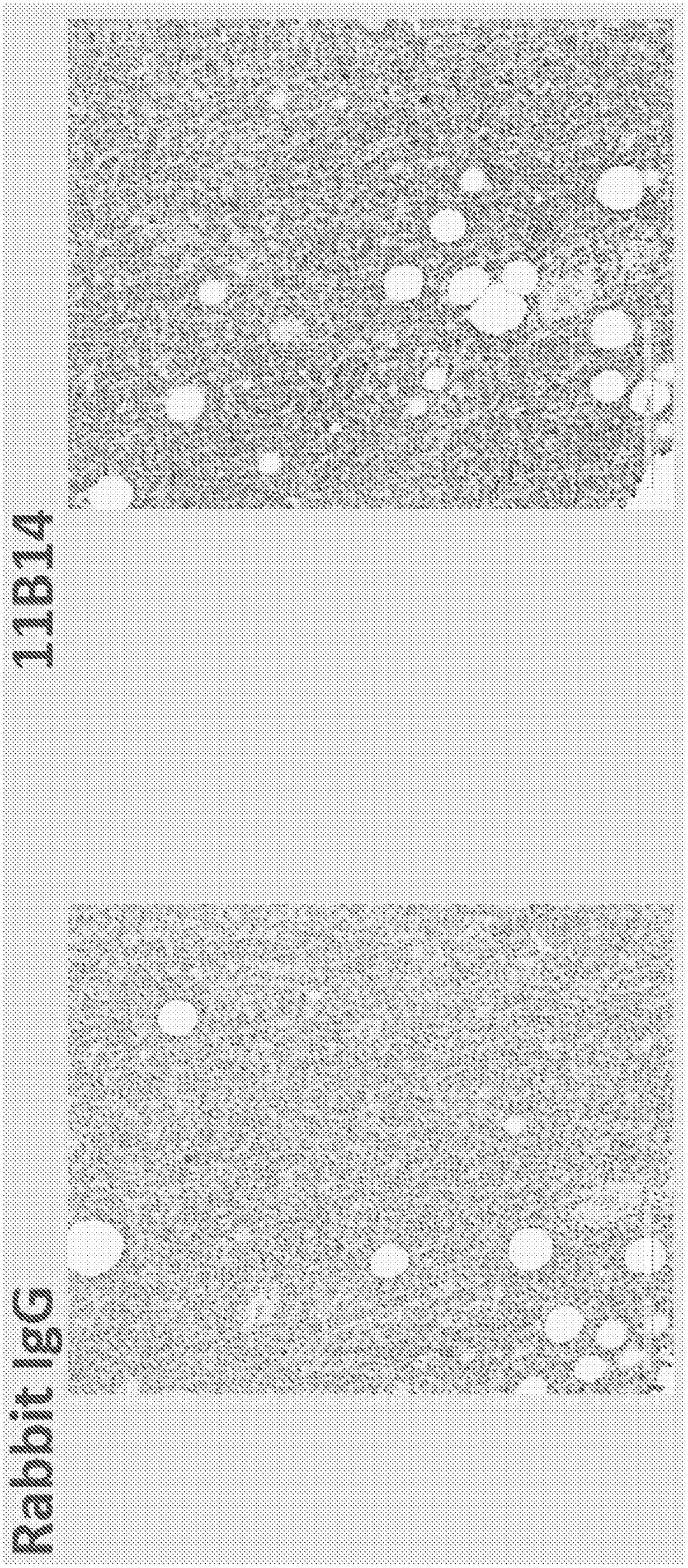
FIG. 15. Comparative antibody binding. Left panel: Bone marrow cells of patient 04H-391 were subjected to immunohistochemical staining with rabbit isotype control antibodies at 1 μg/ml; B) Bone marrow cells of patient 04H-391 were subjected to immunohistochemical staining with anti-Mcl-1 antibody 11B14 at 0.5 μg/ml.
Figure 16:
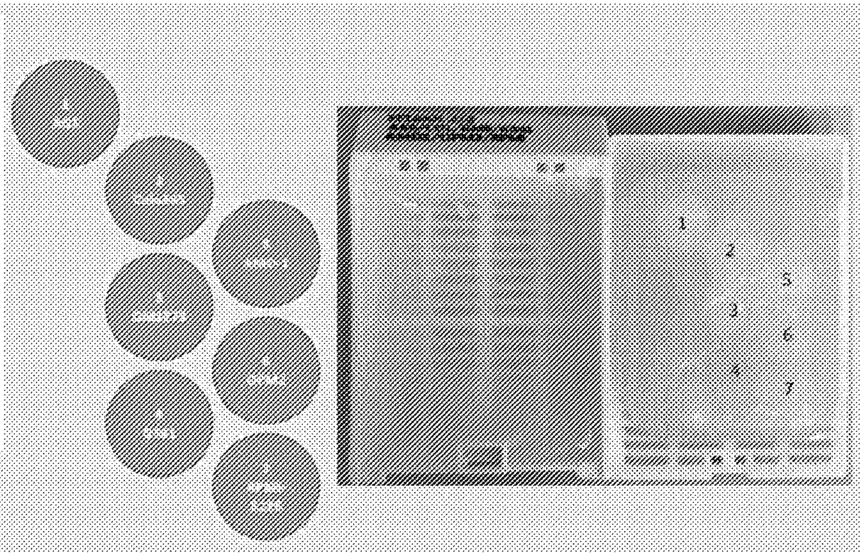
FIG. 16. Expression analysis. The expression levels of Mcl-1, Bcl-2 and Bcl-xL were measured in eight tumor cell lines using monoclonal antibodies identified in Example 6. The results shown in the figure reveal the technique utilized to compare all cell lines on a single analysis, and show the rank-ordered levels of expression of Mcl-1, Bcl-2, and Bcl-xL in the cell lines.
Figure 17:
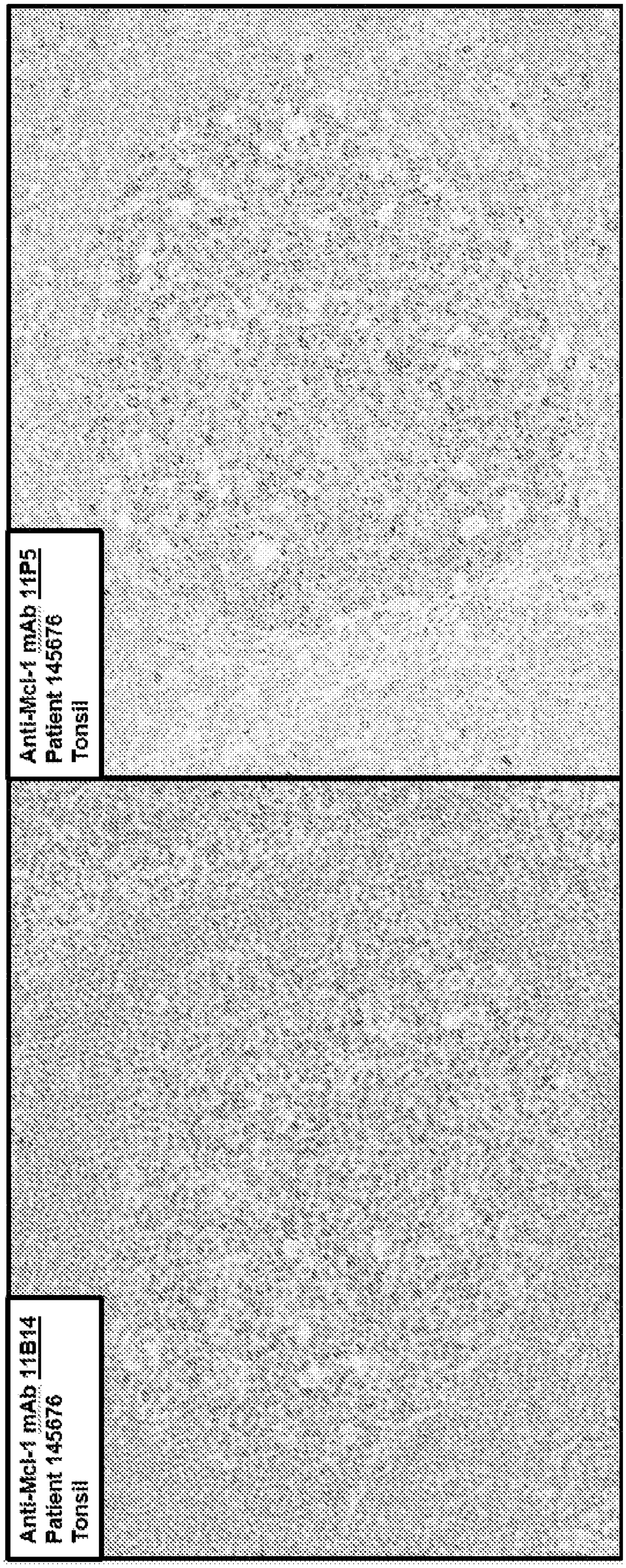
FIG. 17. Immunohistochemical staining of intracellular structures by anti-Mcl-1 antibodies. Left Panel: Tonsil tissue from patient 145676 was probed with anti-Mcl-1 monoclonal antibody 11B14. Right Panel: Tonsil tissue of patient 145676 was probed with anti-Mcl-1 monoclonal antibody 11P5. IHC results revealed that both anti-Mcl-1 antibodies predominantly stained germinal center lymphocytes.
Figure 18:
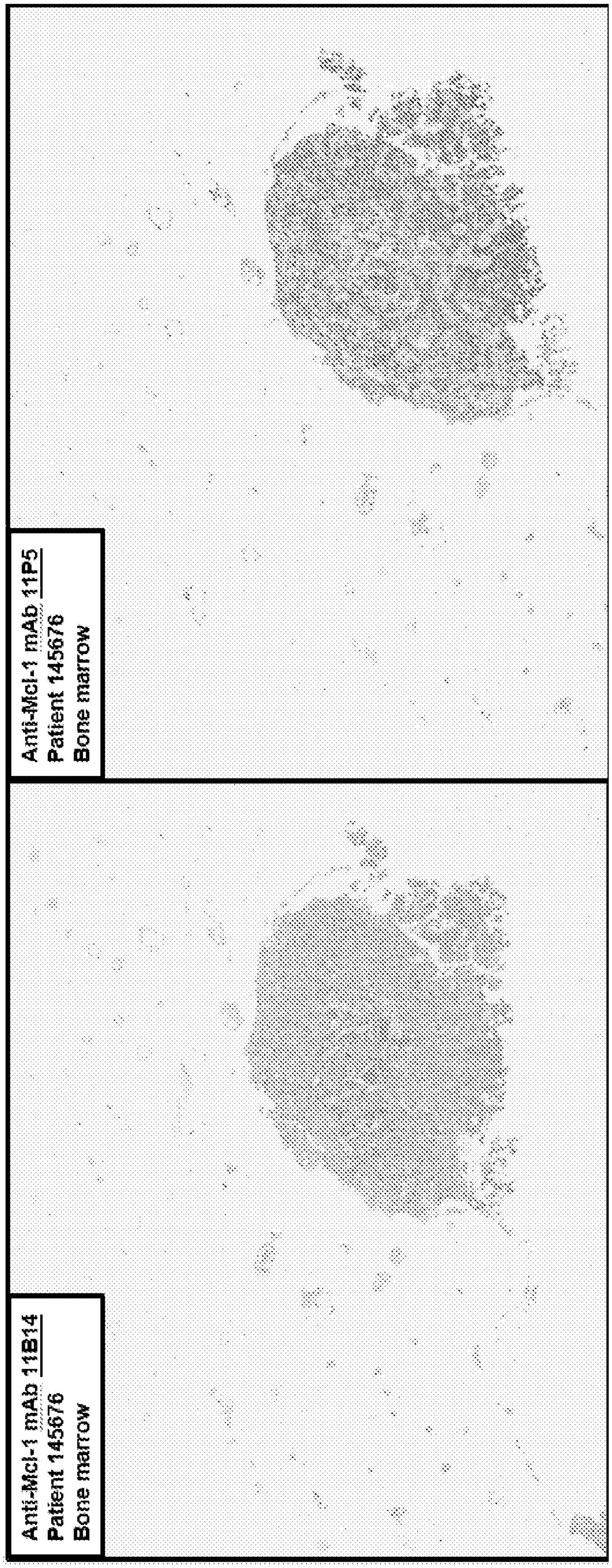
FIG. 18. Differential staining of myeloma cells in bone marrow. Left Panel: Bone marrow cells of patient 145676 were probed with anti-Mcl-1 antibody 11B14. Right Panel: Bone marrow cells of patient 145676 were probed with anti-Mcl-1 antibody 11P5. Results showed that monoclonal anti-Mcl-1 antibody 11P5, but not monoclonal anti-Mcl-1 antibody 11B14, exhibited specific cytoplasmic staining of bone marrow myeloma cells.
Figure 19:
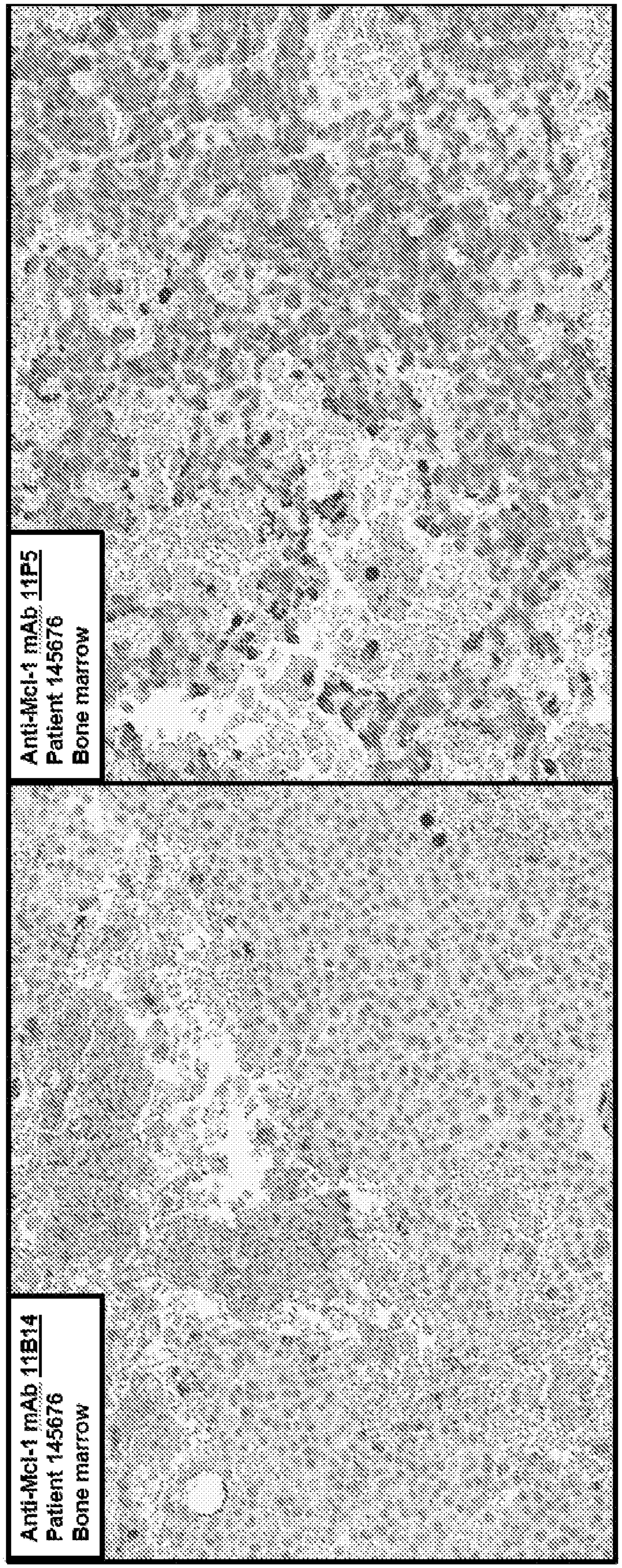
FIG. 19. Differential staining of myeloma cells in bone marrow. Left Panel: Bone marrow cells of patient 145676 were probed with anti-Mcl-1 antibody 11B4. Right Panel: Bone marrow cells of patient 145676 were probed with anti-Mcl-1 antibody 11P5. Results showed that monoclonal anti-Mcl-1 antibody 11P5, but not monoclonal anti-Mcl-1 antibody 11B14, exhibited specific cytoplasmic staining of bone marrow myeloma cells.
Figure 20:
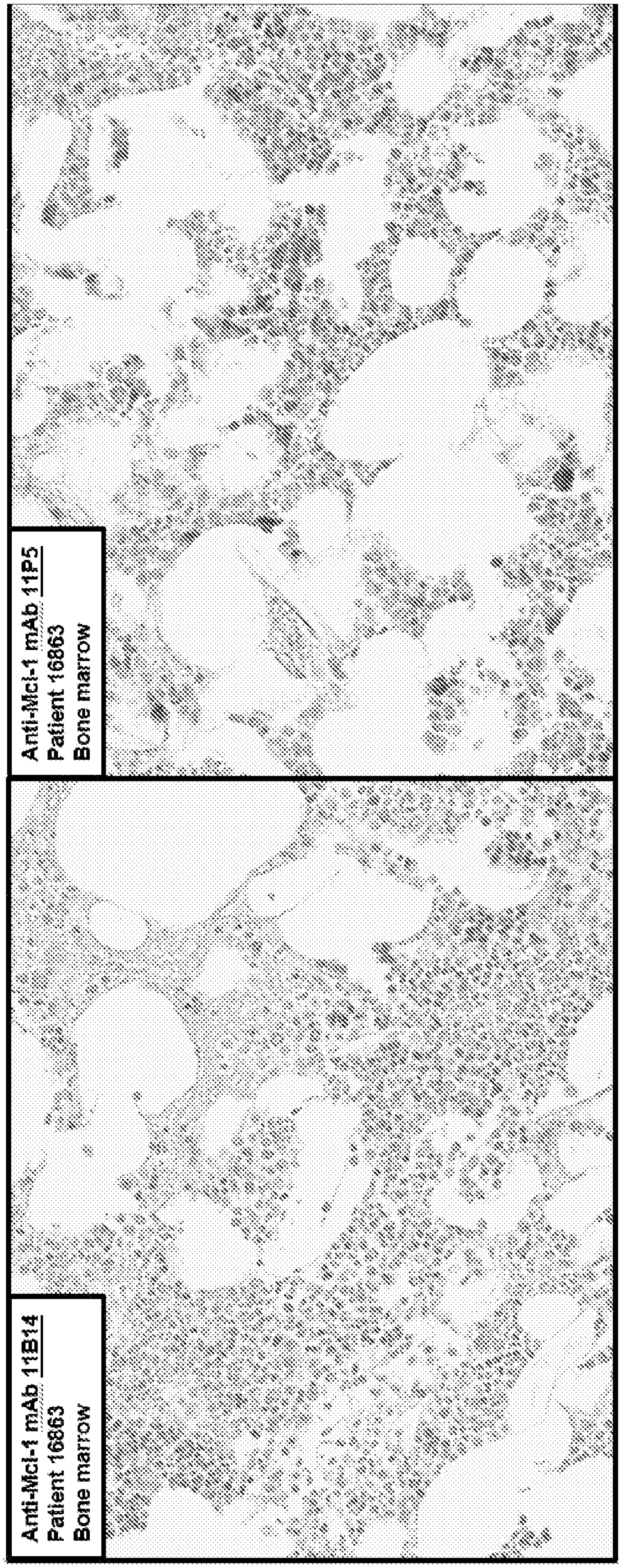
FIG. 20. Differential staining of myeloma cells in decalcified bone marrow. Left Panel: Decalcified bone marrow cells of patient 16863 were probed with anti-Mcl-1 antibody 11B14 and resultant FFPE-processed myeloma cells were subjected to IHC analysis. Right Panel: Decalcified bone marrow cells of patient 16863 were probed with anti-Mcl-1 antibody 11P5 and resultant FFPE-processed myeloma cells were subjected to IHC analysis. Results showed that monoclonal anti-Mcl-1 antibody 11P5, but not monoclonal anti-Mcl-1 antibody 11B14, exhibited specific cytoplasmic staining of myeloma cells in decalcified FFPE-treated bone marrow.
Figure 21:
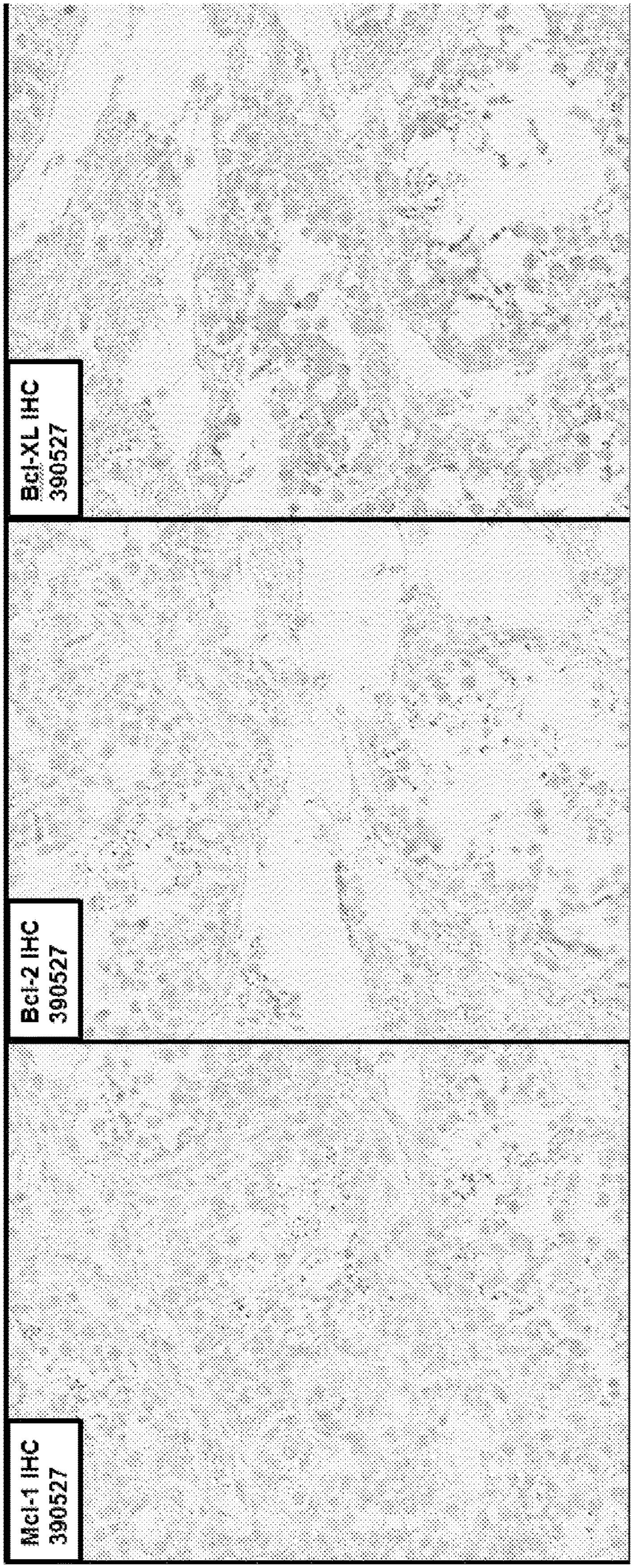
FIG. 21. Assessment of negative control for IHC assays. Left Panel: Cells from the testis tissue of patient 390527 were probed with anti-Mcl-1 monoclonal antibody 11P5 in an IHC assay. Central Panel: Cells from the testis tissue of patient 390527 were probed with an anti-Bcl-2 monoclonal antibody (Agilent DAKO cat. no. M0887) in an IHC assay. Right Panel: Cells from the testis tissue of patient 390527 were probed with an anti-Bcl-xL monoclonal antibody (Cell Signaling Technology cat. no. 2764) in an IHC assay. Results established that cells from human testis provide an appropriate negative control for IHC assays for Mcl-1 and Bcl-2, but not for Bcl-xL.
Figure 22:
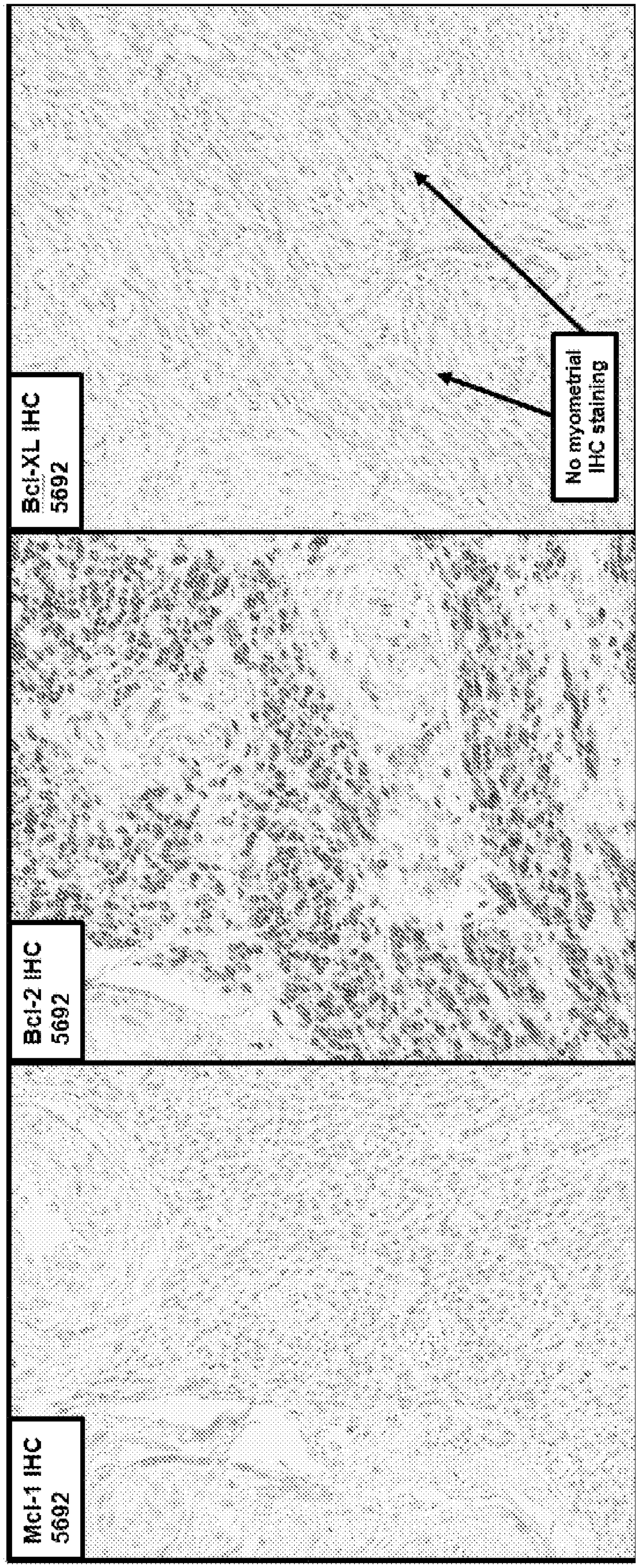
FIG. 22. Assessment of negative control for IHC assays. Left Panel: Cells from the uterus tissue of patient 5692 were probed with anti-Mcl-1 monoclonal antibody 11P5 in an IHC assay. Central Panel: Cells from the uterus tissue of patient 5692 were probed with an anti-Bcl-2 monoclonal antibody (Agilent DAKO cat. no. M0887) in an IHC assay. Right Panel: Cells from the uterus tissue of patient 5692 were probed with an anti-Bcl-xL monoclonal antibody (Cell Signaling Technology cat. no. 2764) in an IHC assay. Results established that cells from human uterus provide an appropriate negative control for IHC assays for Mcl-1, but not for Bcl-2. Results for Bcl-xL showed that Bcl-xL has internal negativity.
Figure 23:
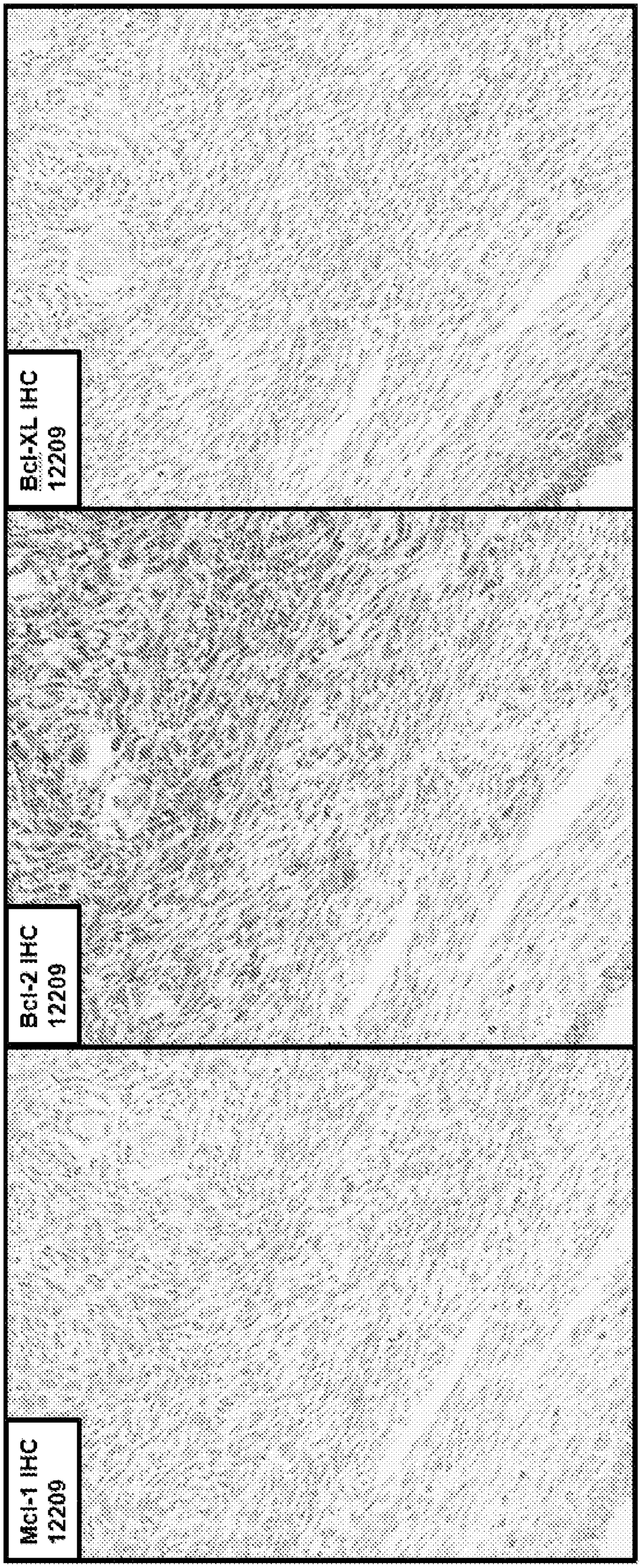
FIG. 23. Assessment of negative control for IHC assays. Left Panel: Cells from the ovary tissue of patient 12209 were probed with anti-Mcl-1 monoclonal antibody 11P5 in an IHC assay. Central Panel: Cells from the ovary tissue of patient 12209 were probed with an anti-Bcl-2 monoclonal antibody (Agilent DAKO cat. no. M0887) in an IHC assay. Right Panel: Cells from the ovary tissue of patient 12209 were probed with an anti-Bcl-xL monoclonal antibody (Cell Signaling Technology cat. no. 2764) in an IHC assay. Results established that cells from human ovary tissue did not provide an appropriate negative control for IHC assays for Mcl-1, Bcl-2, or Bcl-xL.
Figure 24:
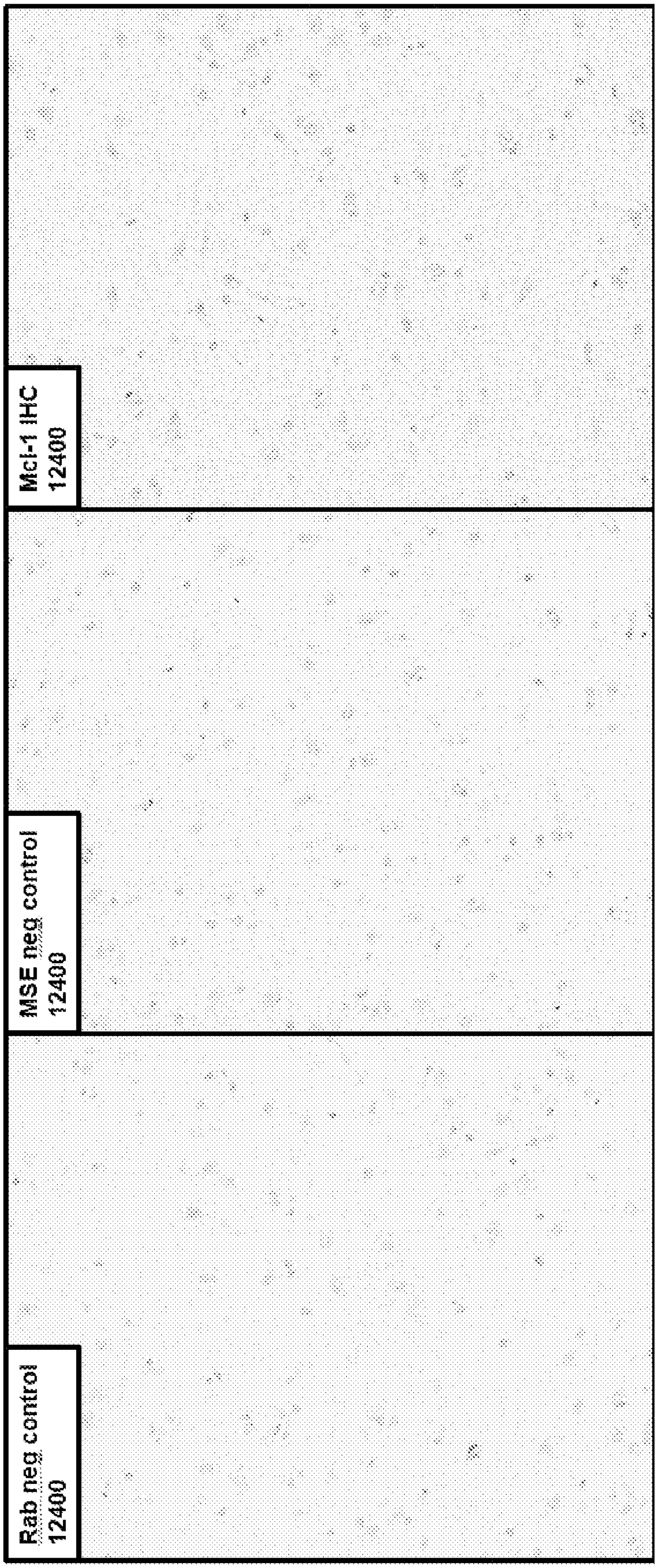
FIG. 24. Assessment of negative control for IHC assays. Left Panel: Cells from the brain tissue of patient 12400 were probed with a rabbit negative control in an IHC assay. Central Panel: Cells from the brain tissue of patient 12400 were probed with a mouse negative control in an IHC assay. Right Panel: Cells from the brain tissue of patient 12400 were probed with an anti-Mcl-1 monoclonal antibody 11P5 in an IHC assay. Results established that cells from human brain were inappropriate for use as a negative control due to background staining.

Eight tumor cell lines were analyzed using anti-Mcl-1 monoclonal antibodies to assess expression levels of Mcl-1 by immunohistochemistry. The results, shown in FIGS. 6-11, demonstrate anti-Mcl-1 antibodies 4019, 5H16, 6A3, 11P5, and 11B14 have immunoreactivity to Mcl-1 in the tumor cells lines. Further, the anti-Mcl-1 antibodies have varying degrees of immunoreactivity relative to the expression level of Mcl-1 in the tumor cell lines, with cell line AMO1 (A in figures) with the highest expression and cell line SKMM2 (H in figures) with the lowest expression (Mcl-1 expression is rank-ordered in FIG. 16). FIGS. 10 and 11 demonstrate antibodies 4019, 11P5, and 11B14 demonstrate stronger immunoreactivity relative to antibodies 5H16 and 6A3 and thus were selected for further characterization in whole tissues. FIGS. 12 and 13 demonstrate that 11P5 and 11B14 (FIG. 12), but not 4019 (FIG. 13), appropriately immunostain tonsillar lymphocytes. FIGS. 14 and 15 demonstrate antibody 11P5 displays stronger immunostaining for Mcl-1 in bone marrow cells (FIG. 14) than antibody 11B14 (FIG. 15). FIGS. 17, 18, 19, and 20 demonstrate antibody 11P5 is superior to 11B14 in detecting Mcl-1 by immunohistochemistry in lymphoid tissue (tonsil and bone marrow, FIGS. 17-19), as well as in decalcified tissue (bone marrow, FIG. 20).

What is claimed is:

1. An anti-Mcl-1 antibody or antigen-binding fragment thereof comprising the light chain complementarity determining region 1 (LCDR1) of SEQ ID NO:4, the light chain complementarity determining region 2 (LCDR2) of SEQ ID NO:5, the light chain complementarity determining region 3 of (LCDR3) SEQ ID NO:6, the heavy chain complementarity determining region 1 of SEQ ID NO:16 (HCDR1), the heavy chain complementarity determining region 2 of SEQ ID NO:17 (HCDR2), and the heavy chain complementarity determining region 3 of SEQ ID NO:18 (HCDR3), or comprising LCDR1 of SEQ ID NO:10, LCDR2 of SEQ ID NO:11, LCDR3 of SEQ ID NO:12, HCDR1 of SEQ ID NO:22, HCDR2 of SEQ ID NO:23, and HCDR3 of SEQ ID NO:24.

2. The antibody of claim 1 comprising the light chain variable region sequence of SEQ ID NO:27 or SEQ ID NO:31, or comprising the heavy chain variable region sequence of SEQ ID NO: 28 or SEQ ID NO: 32.

3. The antibody of claim 2 further comprising the light chain variable region sequence of SEQ ID NO:27 if the heavy chain variable region sequence is set forth in SEQ ID NO:28, or SEQ ID NO:31 if the heavy chain variable region sequence is set forth in SEQ ID NO:32.

4. The antibody or fragment of claim 1 wherein the antibody or fragment is a single-chain antibody or fragment.

5. The antibody fragment of claim 4, wherein the antibody fragment is (a) a scFv;

(b) a Fab; or (c) a (Fab')2.

6. The antibody or fragment thereof of claim 1, which is humanized.

7. The antibody or fragment thereof of claim 1 that is an immunoglobulin G (IgG) isotype antibody or fragment.

8. The antibody or fragment thereof of claim 1 in the form of a monoclonal antibody.

9. The antibody or fragment thereof of claim 1 in the form of a bispecific antibody, a trispecific antibody, a single chain variable fragment (scFv), a disulfide-bond-stabilized single chain variable fragment (ds-scFv), a single domain antibody (sdAb), a single chain Fab fragment (scFab), a diabody, a triabody, a tetrabody, a minibody, a Fab, a $F(ab')_2$, a VHH/VH fragment, a peptibody, a chimeric antigen receptor (CAR), or a bispecific T-cell engager (BITE).

10. A pharmaceutical composition comprising a pharmaceutically acceptable carrier and a therapeutically effective amount of the antibody or an antigen-binding or an immunologically functional immunoglobulin fragment thereof of claim 1.

11. A method of monitoring treatment of a cancer cell in a subject comprising:

(a) contacting the cell of the subject with the antibody or fragment thereof of claim 1;

(b) detecting binding of the antibody or fragment thereof to the cell or its contents;

(c) determining the level of Mcl-1 in the cell; and (d) comparing the level of Mcl-1 in the cell to a control, wherein the control is a known level of Mcl-1 characteristic of a non-cancer cell, a level of Mcl-1 in a non-cancerous cell of the subject, or a level of Mcl-1 in a cancer cell of the subject at a different point in time.

12. The method of claim 11 wherein the monitoring comprises an assay that is an ELISA, a competitive ELISA, surface plasmon resonance analysis, in vitro neutralization assay, in vivo neutralization assay, an immunohistochemical assay with FACS sorting, or an immunohistochemical assay without FACS sorting.

13. The method of claim 11 wherein the cancer cell is a leukemia cell, a lymphoma cell, er a myeloma cell, a myeloid leukemia cell, or an organ cancer cell.

14. The method of claim 13 wherein the cancer treatment comprises administration of AMG 176 of formula I:

I

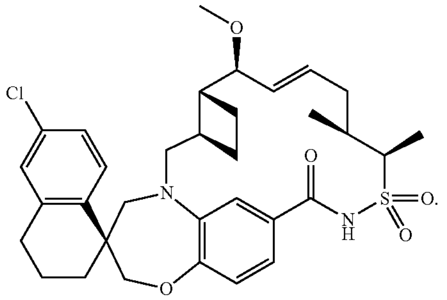

or AMG 397 of formula II

II

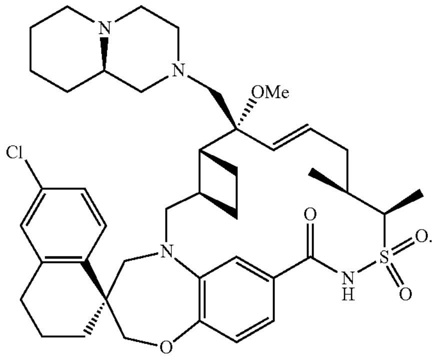

15. The method of claim 13 wherein the antibody or fragment thereof is a monoclonal antibody or fragment thereof comprising;

(a) the light chain complementarity determining region 1 (LCDR1) of SEQ ID NO: 4, the light chain complementarity determining region 2 (LCDR2) of SEQ ID NO: 5, the light chain complementarity determining region 3 (LCDR3) of SEQ ID NO:6, the heavy chain complementarity determining region 1 (HCDR1) of SEQ ID NO:16, the heavy chain complementarity determining region 2 (HCDR2) of SEQ ID NO:17, and the heavy chain complementarity determining region 3 (HCDR3) of SEQ ID NO:18;

(b) the antibody or fragment thereof is a monoclonal antibody or fragment thereof comprising the LCDR1 of SEQ ID NO:10, the LCDR2 of SEQ ID NO: 11, the LCDR3 of SEQ ID NO:12, the HCDR1 of SEQ ID NO:22, the HCDR2 of SEQ ID NO:23, and the HCDR3 of SEQ ID NO:24; or (c) the light chain variable region sequence of SEQ ID NO: 27, the heavy chain variable region sequence of SEQ ID NO: 28, or the light chain variable region of SEQ ID NO: 31 and the heavy chain variable region of SEQ ID NO: 32.

16. The method of claim 13 wherein the antibody or fragment thereof is in the form of a single-chain antibody, a single-chain variable fragment (scFv), a scFv, a Fab, a F(ab')2, a bispecific antibody, a trispecific antibody, a single chain variable fragment (scFv), a disulfide-bond-stabilized single chain variable fragment (ds-scFv), a single domain antibody (sdAb), a single chain Fab fragment (scFab), a diabody, a triabody, a tetrabody, a minibody, a Fab, a $F(ab')_2$, a VHH/VH fragment, a peptibody, a chimeric antigen receptor (CAR), or a bispecific T-cell engager (BiTE).

17. A method of treating cancer in a subject comprising administering a therapeutically effective amount of the anti-Mcl-1 antibody or fragment thereof of claim 1 to the subject.

18. The method of claim 17 wherein the cancer cell is a leukemia cell, a lymphoma cell, or a myeloma cell, a myeloid leukemia cell, or an organ cell.

19. The method of claim 17 wherein the antibody or fragment thereof is a monoclonal antibody or fragment thereof comprising:

(a) the light chain complementarity determining region 1 (LCDR1) of SEQ ID NO: 4, the light chain complementarity determining region 2 (LCDR2) of SEQ ID NO: 5, the light chain complementarity determining region 3 (LCDR3) of SEQ ID NO:6, the heavy chain complementarity determining region 1 (HCDR1) of SEQ ID NO:16, the heavy chain complementarity determining region 2 (HCDR2) of SEQ ID NO:17, and the heavy chain complementarity determining region 3 (HCDR3) of SEQ ID NO:18;

(b) the antibody or fragment thereof is a monoclonal antibody or fragment thereof comprising the LCDR1 of SEQ ID NO:10, the LCDR2 of SEQ ID NO: 11, the LCDR3 of SEQ ID NO:12, the HCDR1 of SEQ ID NO:22, the HCDR2 of SEQ ID NO:23, and the HCDR3 of SEQ ID NO:24; or (c) the light chain variable region sequence of SEQ ID NO: 27, the heavy chain variable region sequence of SEQ ID NO: 28, or the light chain variable region of SEQ ID NO: 31 and the heavy chain variable region of SEQ ID NO: 32.

20. The method of claim 17 wherein the antibody or fragment thereof is in the form of a single-chain antibody, a single-chain variable fragment (scFv), a scFv, a Fab, a F(ab')2, a bispecific antibody, a trispecific antibody, a single chain variable fragment (scFv), a disulfide-bond-stabilized single chain variable fragment (ds-scFv), a single domain antibody (sdAb), a single chain Fab fragment (scFab), a diabody, a triabody, a tetrabody, a minibody, a Fab, a $F(ab')_2$, a VHH/VH fragment, a peptibody, a chimeric antigen receptor (CAR), or a bispecific T-cell engager (BiTE).

* * * * *